US012070371B2

(12) United States Patent
Silver et al.

(10) Patent No.: US 12,070,371 B2
(45) Date of Patent: *Aug. 27, 2024

(54) TEMPORARY TOOTH REPAIR/TREATMENT COMPOSITION AND METHODS OF USE THEREOF

(71) Applicant: OrVance, LLC, Caledonia, MI (US)

(72) Inventors: Michael Edward Silver, Lake City, MI (US); Charles Schryver, Atascadero, CA (US); Ronald J. Schutt, Ludington, MI (US)

(73) Assignee: OrVance, LLC, Caledonia, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/123,684

(22) Filed: Mar. 20, 2023

(65) Prior Publication Data

US 2023/0248477 A1    Aug. 10, 2023

Related U.S. Application Data

(63) Continuation-in-part of application No. 17/720,270, filed on Apr. 13, 2022, now Pat. No. 11,607,371, which is a continuation-in-part of application No. 17/665,259, filed on Feb. 4, 2022, now Pat. No. 11,622,834.

(51) Int. Cl.
*A61C 8/00*    (2006.01)

(52) U.S. Cl.
CPC .......... *A61C 8/0013* (2013.01); *A61C 8/0087* (2013.01)

(58) Field of Classification Search
CPC .................................................... A61K 6/884
See application file for complete search history.

(56) References Cited

U.S. PATENT DOCUMENTS

| 3,455,872 A | 7/1969 | Beck |
| 4,497,926 A | 2/1985 | Toy |
| 4,503,116 A | 3/1985 | Lapidus |
| 4,529,748 A | 7/1985 | Wienecke |

(Continued)

FOREIGN PATENT DOCUMENTS

| CA | 2858830 A1 | 6/2013 |
| EP | 2544651 A1 | 1/2013 |

(Continued)

OTHER PUBLICATIONS

KJ Chun et al., "Comparison of mechanical property and role between enamel and dentin in the human teeth," Journal of Dental Biomechanics, May 9, 2013, 7 pages.

(Continued)

*Primary Examiner* — Michael F Pepitone
(74) *Attorney, Agent, or Firm* — Nyemaster Goode P.C.

(57) ABSTRACT

A hygienically packaged composition that includes a base layer of a thermoplastic film, a covering film layer that is a heat sealable or pressure sealable adhesive liner that covers the hygienically packaged composition where the hygienically packaged composition is a dental composition, a food composition, or a medicine. The covering film layer includes a stretched dimple in a portion of the covering film layer proximate the hygienically packaged composition thereunder the covering film layer. There is typically a heat or pressure seal around each hygienically packaged composition.

20 Claims, 15 Drawing Sheets

(56) References Cited

U.S. PATENT DOCUMENTS

| | | |
|---|---|---|
| 4,801,475 A | 1/1989 | Halpern et al. |
| 4,957,783 A | 9/1990 | Gabryszewski |
| 5,624,745 A | 4/1997 | Lapidus |
| 5,700,478 A | 12/1997 | Biegajski et al. |
| 5,938,435 A | 8/1999 | Raspino, Jr. |
| 6,447,290 B1 | 9/2002 | Williams |
| 6,638,881 B2 | 10/2003 | Lapidus |
| 7,195,484 B1 | 3/2007 | Wagner |
| 7,312,256 B2 | 12/2007 | Borja |
| 7,789,662 B2 | 9/2010 | Van Eikeren et al. |
| 8,007,277 B2 | 8/2011 | Fischer et al. |
| 8,936,026 B2 | 1/2015 | Hannapel et al. |
| 9,375,292 B2 | 6/2016 | Peuker et al. |
| 9,987,102 B2 | 6/2018 | Hannapel et al. |
| 9,987,103 B1 | 6/2018 | Hannapel et al. |
| 10,391,040 B1 | 8/2019 | Schutt et al. |
| 11,083,544 B1 | 8/2021 | Silver et al. |
| 11,607,371 B1 * | 3/2023 | Silver .................... A61K 6/887 |
| 2003/0205234 A1 | 11/2003 | Bardach et al. |
| 2004/0202983 A1 | 10/2004 | Tricca et al. |
| 2005/0089820 A1 | 4/2005 | Allred et al. |
| 2005/0181324 A1 | 8/2005 | Hare |
| 2005/0239015 A1 | 10/2005 | Dragan |
| 2006/0063128 A1 | 3/2006 | Dragan |
| 2007/0015107 A1 | 1/2007 | Mannschedel et al. |
| 2007/0185237 A1 | 8/2007 | Rajaiah et al. |
| 2008/0085493 A1 | 4/2008 | Sun et al. |
| 2008/0293015 A1 | 11/2008 | Wong et al. |
| 2009/0087809 A1 | 4/2009 | Jessop et al. |
| 2011/0315151 A1 | 12/2011 | Schabert |
| 2012/0107768 A1 | 5/2012 | Diedwardo |
| 2012/0199138 A1 | 8/2012 | Hannapel et al. |
| 2014/0017637 A1 | 1/2014 | Cinader, Jr. et al. |
| 2015/0037266 A1 | 2/2015 | Boyd et al. |
| 2015/0209120 A1 | 7/2015 | Hannapel et al. |
| 2015/0297550 A1 | 10/2015 | Jay |

FOREIGN PATENT DOCUMENTS

| | | |
|---|---|---|
| EP | 2698171 A1 | 2/2014 |
| WO | 2011112193 A1 | 9/2011 |
| WO | 2012109174 A2 | 8/2012 |
| WO | 2013130552 A1 | 9/2013 |

OTHER PUBLICATIONS

Laura Dorr, "Key differences between bonding to dentin versus enamel," Dental Products Report, May 20, 2020, 3 pages.

Nisha Garg et al., "Textbook of Operative Dentistry", Chapter 16—Bonding to Enamel and Dentin, Jan. 1, 2020, pp. 237-254.

NuSil MED-4174 Silicone, One Part High Consistent Elastomer—Restricted Medical Use, MatWeb, www.matweb.com/search/datasheettext.aspx?matguid=4e4cdf84847c4806bc411e66e9416a7f. (Year 2020).

* cited by examiner

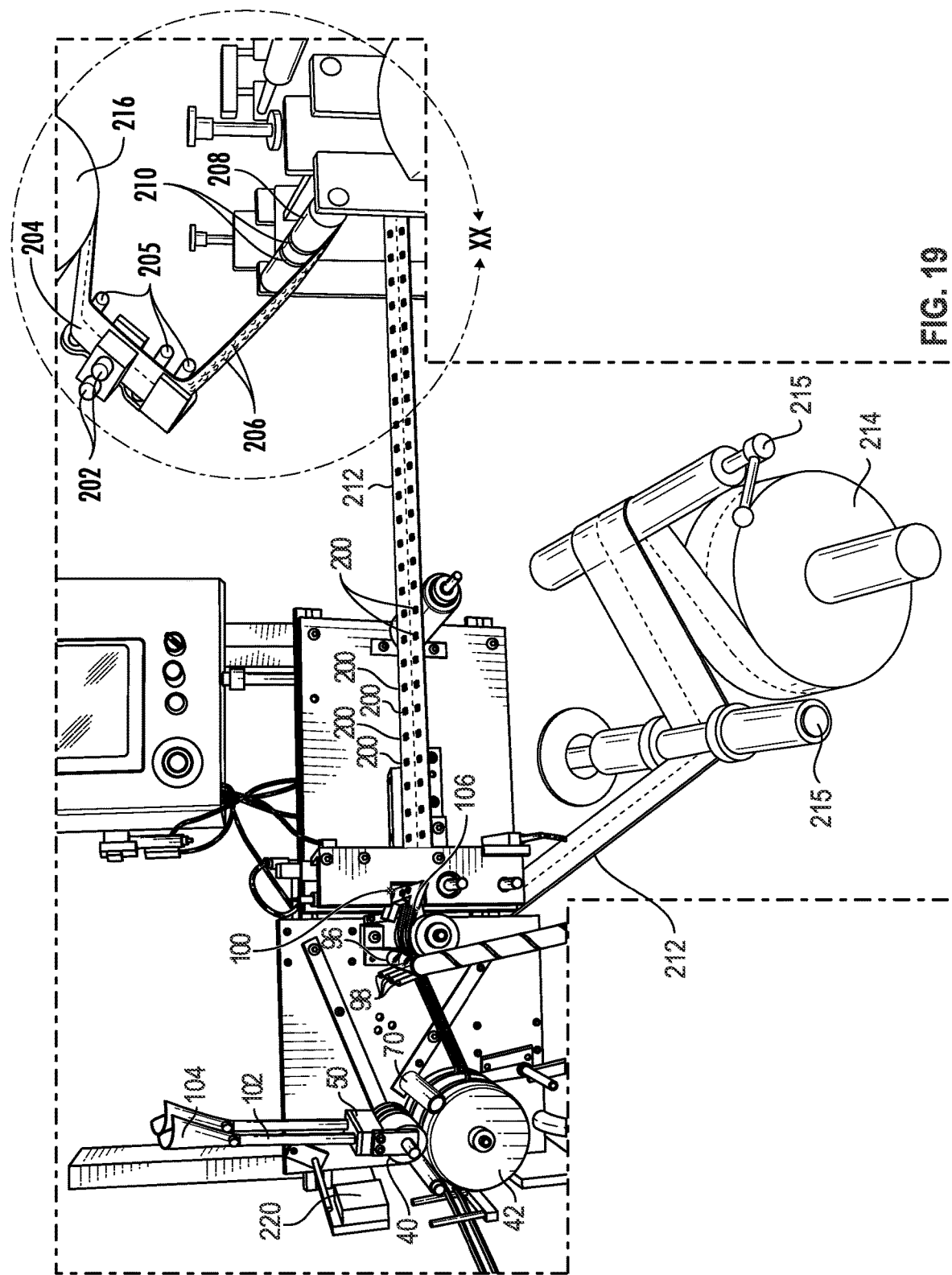

TEMPORARY TOOTH REPAIR/TREATMENT COMPOSITION AND METHODS OF USE THEREOF

CROSS-REFERENCE TO RELATED APPLICATION

This application is a continuation-in-part of and claims priority to U.S. patent application Ser. No. 17/720,270 is now U.S. Pat. No. 11,607,371, filed on Apr. 13, 2022, entitled "TEMPORARY TOOTH REPAIR/TREATMENT COMPOSITION AND METHODS OF USE THEREOF." U.S. patent application Ser. No. 17/720,270 is a continuation-in-part of and claims priority to U.S. patent application Ser. No. 17/665,259 is now U.S. Pat. No. 11,622,834, filed on Feb. 4, 2022, entitled "TEMPORARY TOOTH REPAIR/TREATMENT COMPOSITION AND METHODS OF USE THEREOF." The disclosures of each of the above applications are hereby incorporated herein by reference in their entirety.

BACKGROUND

People and other animals with teeth often suffer from sensitive teeth or damaged teeth that cause a varying degree of discomfort to outright pain. Prior compositions such as the DENTEMP® Loose Cap & Lost Filling Repair product have attempted to help alleviate the pain of a broken tooth or lost filling where a nerve is accessible or exposed and very sensitive to even air. That compositions includes calcium sulfate, barium sulfate, dimethoxytetraethylene glycol, zinc oxide, eugenol, and ethylmethacrylate polymer. Eugenol is a potential allergen. Additionally, the composition is difficult for a layperson to apply and use effectively. Their instructions are complex and require that the composition be applied to a wet tooth and that the wearer wait at least two hours before eating to allow the composition to set. In fact, the instructions further require that the crown be prepared by carefully removing as much old cement as possible from inside the crown. The crown should be rinsed with water and must be left moist. Next, the existing Loose Cap & Lost Filling Repair Product requires that the person check and see if the crown will fit on the tooth and, if not, the user can't proceed to use this product. If it does, a small amount of material, which must be removed from its small container having a small opening with the included tool (the container must be properly resealed or the remaining product will degrade in short order) and applied in a very small amount to the interior of the crown. The crown is then pressed on the wet tooth and bitten down upon. If the fit is not good the crown must be removed and the entire process repeated. When the DENTEMP® Loose Cap & Lost Filling Repair product is used to replace a lost filling, the applicator tool is used to remove a small amount of material from the vial, form it into a ball with wet fingers and pressed firmly into the cavity. Next, the person needs to scrape the material off of his/her finger by scraping a finger along the edge of the tooth. The instructions specifically state that one should not lift their finger straight up as this might loosen the material in the cavity. The wearer should bite down several times to insure proper bite. The instructions specifically also state that the wearer must allow two (2) hours to set before eating.

The DENTEMP® Cap & Crown Repair product is similar. This product contains calcium Sulfate, dimethoxytetraethylene glycol, zinc oxide, potassium sulfate, ethylmethacrylate polymer, and triacetin. The composition is delivered in a small tube. As with the Loose Cap & Lost Filling Repair, the instructions are complex. First, the crown must be prepared by carefully removing as much old cement as possible from inside the crown. The crown should next be rinsed well. The tooth area should be cleaned and rinsed with water and must be left moist. The crown is then placed back on the tooth before applying new material. This is done to make sure it fits properly. If one cannot do this, the material may not be used and the user of the composition should not proceed and instead exclusively see his/her dentist. If it does fit, the next step is to ensure that the inside of the crown is dry. The tube containing the composition is opened by reversing the cap and punching a hole in the tip of the tube. Thereafter, a small amount of material is applied onto the upper inside edge of the crown. The tooth area is remoistened, the crown placed on the wet, remoistened tooth and pressed firmly into position. The wearer is instructed to bite down several times to ensure a proper fit. If the bite is not completely comfortable, the crown should be removed and the process repeated until the crown feels normal. After 5 minutes, the person must gently remove any excess material and rinse his/her mouth out with water. The instructions further require at least 1 hour to set the composition before eating and specifically state that the cement will fully set in 1 to 3 hours. Another similar product is DENTEK® TEMPARIN® Max Repair Kit. As with all such temporary over the counter dental cements, the product requires wetting by saliva and an appreciable amount of time (typically 1-3 hours) for it to harden and set—especially before eating or drinking. When used to cover a missing filling or broken tooth, these temporary cements often produce foul tastes and loose pieces of dental cement before and after hardening which require spitting out or are often swallowed, and the resulting hardened cement is uncomfortably rough to the tongue and surrounding mucosal tissues.

SUMMARY

The compositions of the present disclosure do not require excess wait times for relief or complex instructions to safely and accurately apply the materials and achieve the results desired for providing temporary relief from broken teeth, lost fillings, caps and crowns. There is no time needed to wait for the pliable, moisture-activated adhesive containing compositions of the present disclosure to set. Moreover, they are easy to apply, are typically tooth colored, are individually and hygienically packaged, and do not have a foul taste in one's mouth. The compositions of the present disclosure also provide a shielded occlusive effective treatment that is safely and easily applied to a surface of the teeth to deliver active ingredients to provide pain relief from sensitive teeth or lessen pain from sensitive teeth.

An aspect of the present disclosure is generally directed to a temporary tooth repair composition, which is a dental composition, that includes a combination of an uncured, uncrosslinked silicone high consistency rubber base material and at least one metal oxide pigment mixed therein and an adhesive on at least one exterior surface of the temporary tooth repair composition such that finger force applied to the temporary tooth repair composition adheres the temporary tooth repair composition to a surface of a broken tooth. The temporary tooth repair composition may be shaped using fingers and/or the tooth on an opposing side of the mouth such that when the temporary tooth repair composition engages the surface of the broken tooth, the combined broken tooth and temporary tooth repair composition mimic the natural shape and size of the broken tooth prior to the broken tooth being broken. The temporary tooth repair composition typically adheres to the broken tooth within 8 seconds or less of being applied to the broken tooth using finger pressure and adheres for at least four hours, more typically at least 8 hours.

Another aspect of the present disclosure is generally directed to a packaged dental composition that includes: a layer of a thermoplastic film, a covering film that is a heat sealable or pressure sealable adhesive liner that covers a dental composition and a seal around an individual use dosage of the dental composition. The dental composition may be chosen from: an extrudable dental cement composition that is extrudable through a die at a temperature of from about 10° C. to about 50° C. and an extrudable base material that is extrudable through a die at a temperature of from about 10° C. to about 100° C. The extrudable base material typically includes at least one of the following compounds: (A) a product consisting of one or more hydrocarbon-based waxes and optionally also one or more inorganic filler, one or more organic filler, or one or more inorganic and organic fillers; (B) an uncured, uncrosslinked silicone high consistency rubber base; and (C) a hydrophobic water insoluble solid material that is malleable at 37° C. or lower and safe for a human oral environment. The extrudable base material typically has a surface composition applied thereon. The surface composition may include at least one dry, powdered hydrophilic polymeric substance engaged with and dispersed on one or more surface of the extrudable base material and optionally a desensitizing agent.

Yet another aspect of the present disclosure includes at least one individually sealed dental composition that includes a layer of a thermoplastic film; a covering film that is a heat sealable or pressure sealable adhesive liner that covers a dental cement composition; a seal around an individual use dosage of the dental cement composition. The extrudable dental cement composition is extrudable through a die at a temperature of from about 10° C. to about 50° C. The dental cement composition may have a textured or non-textured surface thereon and the at least one dry, powdered hydrophilic polymeric substance is typically engaged, typically mechanically engaged, with and dispersed on the textured or non-textured surface of the dental cement composition.

Another aspect of the present disclosure is generally directed toward at least one individually sealed dental composition that includes: a base layer that is a thermoplastic film; a covering film having a surface area wherein the covering film is a heat sealable or pressure sealable adhesive liner that covers a dental cement composition and having a dimpled portion of surface area positioned over the dental cement composition; and a hygienic seal around the dental cement composition. The extrudable dental cement composition is extrudable through a die at a temperature of from about 10° C. to about 50° C. The dental cement composition may have a coating composition applied to at least one surface thereof that includes a desensitizing component and at least one dry, powdered hydrophilic polymeric component that is chosen from the group consisting of: a polyvinylpyrrolidone, a polyoxazoline, a polyethylene glycol, a starch, a polyacrylic acid, a carbomer, a polyvinyl alcohol, a polyvinyl acetate, a cellulose derivative, a polysaccharide, a polyacrylamide, a N-vinyl caprolactam polymer, a copolymer of methyl vinyl ether and maleic anhydride (PVM/MA), and blends thereof.

Another aspect of the present disclosure generally includes a hygienically packaging a dental composition, a medicine, or a food composition comprising a base layer with a perimeter portion and an interior portion and a top layer having a perimeter portion and an interior portion wherein the interior portion of the base layer, the interior portion of the top layer, or both are flexed to create a thinner film portion and wherein the perimeter portion of the base layer and the perimeter portion of the top layer are sealed together typically by either heat sealing or pressure sealing the perimeter portion of the top layer and the perimeter portion of the base layer together and wherein the dental composition, the medicine, or the food composition is positioned between the interior portion of the base layer and the top layer.

Yet another aspect of the present disclosure is generally directed toward a method of making a hygienically packaged product chosen from a dental composition, a medicine, or a food composition that includes the steps of: preparing the dental composition, the medicine, or the food composition; applying a stretching force to either a first film or a second film or both to stretch a portion of the interior of the first film, the interior of the second film or both and create at least one flexed portion within the interior of the first film, the second film or both; placing the dental composition, the medicine or the food composition on a surface of a first film or a surface of the second film such that at least one of the flexed portion of the first film and/or the flexed portion of the second film are positioned over the dental composition, the medicine, or the food composition of the hygienically packaged product; sealing by either heat sealing or pressure sealing, the dental composition, the medicine, or the food composition within the interior of the first film and the interior of the second film by either heat sealing or pressure sealing a perimeter area around the dental composition, the medicine or the food composition to form the hygienically packaged product.

The dental composition, the medicine, or the food composition most typically sealed within the hygienically packaging include those that has a propensity to be significantly depressed if a flexed portion or portions are not utilized. Even with the use of one or more flexed portions, some downward force may be applied to the dental composition, the medicine, or the food composition, but significantly less than would otherwise be applied in such a packaging system that does not utilize the flexing of the film layers. In the case of the dental compositions of the present disclosure, when the base material is an uncured, uncrosslinked silicone high consistency rubber base, the material is typically significantly mixed with colorant to create a tooth colored base material, which results in a softer, more pliable base material than if the colorant such as titanium dioxide were not blended therein. The colorant typically is blended with the colorant or other components to be blended with the base material such that a substantially homogenous or homogenous distribution of the additives is created.

The stretching force is applied by passing the first film or the second film through a dimpler, which is typically a pneumatic-driven dimpler that provides at least one piston force to the second film, which is typically over the first film, which is typically a bottom film that receives the dental composition, the medicine, or the food composition before the top film with the flexed portion or portions therein are applied over the dental composition, the medicine, or the food composition.

Another aspect of the present disclosure is generally directed toward a method that includes the step of using a person's fingers to push a dental composition into engagement with a damaged tooth surface of a damaged tooth thereby adhering the dental composition to the damaged tooth surface and covering at least a portion of the damaged tooth surface. The dental composition includes a base material comprising at least one of the following compounds chosen from the group consisting of: a product consisting of one or more hydrocarbon-based waxes that may also include inorganic fillers and/or organic fillers; an uncured, uncrosslinked silicone high consistency rubber base; and a hydrophobic water insoluble solid material that is malleable at 37° C. or lower and safe for a human oral environment. The base material typically has at least one dry, powdered hydrophilic polymeric substance engaged with and dispersed on one or more surface of the base material.

Another aspect of the present disclosure is generally directed toward a method that includes the steps of: removing a dental composition from a single use, hygienically packaged system; and applying a finger force to the dental composition to push the dental composition into engagement with a damaged surface of a person's tooth. The dental composition comprises an extruded base material that is a comprising at least one of the following compounds chosen from the group includes: a product consisting of one or more hydrocarbon-based waxes that may also include inorganic or inorganic fillers; an uncured, uncrosslinked silicone high consistency rubber base; and a hydrophobic water insoluble solid material that is malleable at 37° C. or lower and safe for a human oral environment. The extruded base material has at least one dry, powdered hydrophilic polymeric substance on an exterior surface of the extruded base material.

Yet another aspect of the present disclosure is generally directed to a method that includes the step of: engaging a dental composition with a surface of a damaged tooth within a person's mouth chosen from the group consisting of: a tooth chip, a decayed tooth surface, a tooth cavity, a previously reshaped tooth surface, a tooth pulp cavity, a cracked tooth surface, and combinations thereof. The dental composition includes: a finger malleable base material that includes an uncured, uncross-linked silicone high consistency rubber base and has an exterior surface and wherein exterior surface of the finger malleable base material has at least one dry, powdered hydrophilic polymeric substance on a surface of the extruded base material.

Yet another aspect of the present disclosure includes a kit that has a plurality of sheets where each sheet has a plurality of the single use, hygienically packaged systems conjoined with one another and each of the single use, hygienically packaged systems are openable by hand and without the use of tools.

These and other aspects, objects, and features of the present invention will be understood and appreciated by those skilled in the art upon studying the following specification, claims, and appended drawings.

BRIEF DESCRIPTION OF THE DRAWINGS

In the drawings:

FIG. 19 is a perspective view of an overall assembly system for the production of the temporary tooth repair compositions of the present disclosure having the bottom heat sealing film base rolls of material and the dimpler systems of the overall systems of the present disclosure.

DETAILED DESCRIPTION

Figure 1A:
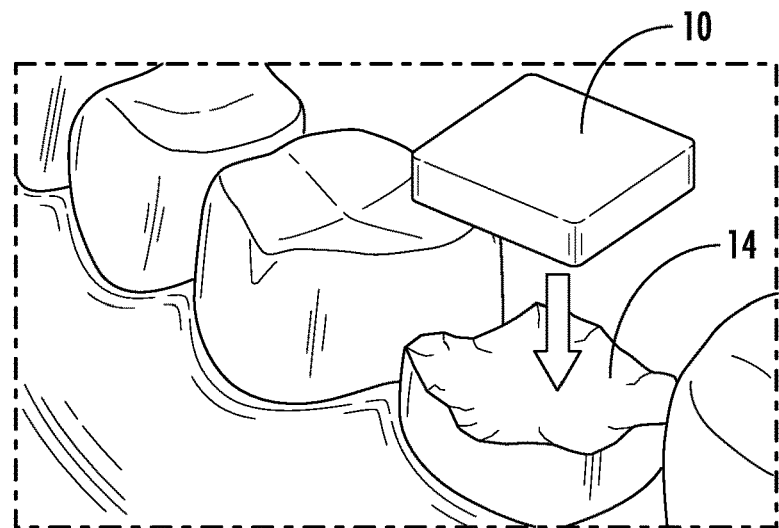
FIG. 1A is an initial perspective view showing an initial stage of installing the temporary tooth repair composition of the present disclosure onto the surface of a broken tooth or with an interior of the tooth exposed to the elements.
Figure 1B:
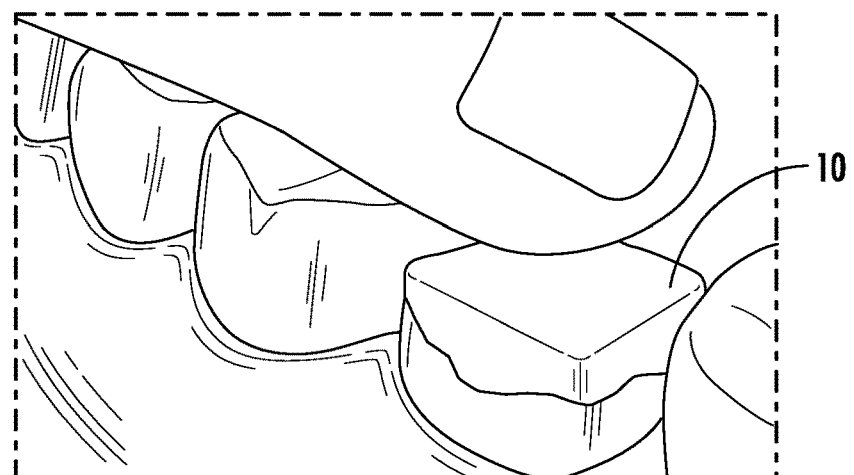
FIG. 1B is an intermediate stage perspective view showing an intermediate stage of installing the temporary tooth repair composition of the present disclosure onto the surface of a broken tooth or over an interior of the tooth exposed to the elements to shield the tooth from the exposure and the often-associated pain of an exposed nerve of a damaged tooth.
Figure 1C:
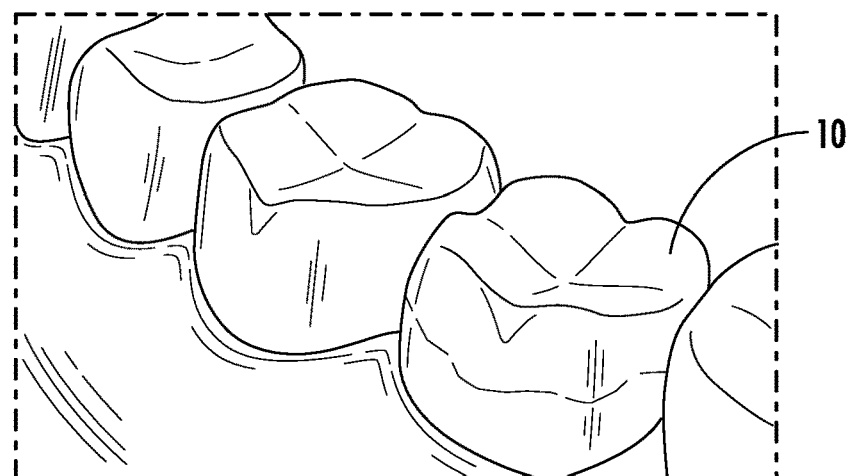
FIG. 1C is an end stage perspective view showing an end stage of installing the temporary tooth repair composition of the present disclosure onto the surface of a broken tooth or over an interior of the tooth exposed to the elements to shield the tooth from the exposure and the often-associated pain of an exposed nerve of a damaged tooth where the temporary tooth repair composition has been formed, typically by hand and without the use of tools.

For purposes of description herein, the terms "upper," "lower," "right," "left," "rear," "front," "vertical," "horizontal," and derivatives thereof shall relate to the invention as oriented in FIGS. 1A-1C. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the scope of the present disclosure. The upper and lower limits of these smaller ranges may independently be included in the smaller ranges, and are also encompassed within the scope of the present disclosure, subject to any specifically excluded limit in the stated range. Where the stated range includes one or both of the limits, ranges excluding either or both of those included limits are also included in the scope of the present disclosure.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

The dental compositions, including the extrudable dental cement compositions and the temporary tooth repair compositions as well as the methods of their use and packaging described in the present disclosure may comprise, consist of, or consist essentially of the elements of the products as described herein, as well as any additional or optional element(s) described herein or otherwise useful dental compositions, including dental cement applications and in temporary tooth repair use applications. Consists essentially of or consisting essentially of mean that the steps, composition or formulation (a) necessarily includes the listed ingredients and (b) is open to unlisted ingredients that do not materially affect the basic and novel properties of the composition such as their ability to adhere for many hours after finger pressure is applied to adhere the tooth repair composition and still allow for finger force removal of the composition from engagement with the tooth, typically a damaged and/or sensitive tooth at any time. In this case, for example, while potentially some amount of cross-linking catalyst could be added to the pliable material employed for the devices of the present disclosure (the pliable material typically but not limited to uncured high consistency silicone elastomer base) and not cross-link the pliable material; however, if an amount of cross-linking catalyst is included in the temporary tooth repair compositions of the present disclosure to substantially or completely cross-link or cure the dental compositions, they materially change the functioning of the composition because its shape is no longer permanently adjustable. Similarly, if an adhesive or adhesives or other non-adhesive component(s) are used in connection with the dental compositions of the present disclosure that will not permit the dental, typically the temporary tooth repair composition to adhere for an extended period of time, but also be removable using finger pressure, then this would materially change the functioning of the composition of the present disclosure.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the Applicant intends to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

Also, as discussed herein tooth means a single tooth and teeth means more than one tooth, but the concepts of the present disclosure and the composites, systems and other disclosed materials of the present disclosure may apply to one or more teeth unless specifically indicated otherwise herein.

As shown in general in FIGS. 1A-1C, the present disclosure is generally directed toward temporary tooth repair compositions, typically a human temporary tooth repair composition 10, and methods of using the temporary tooth repair compositions by a non-dental professional or a dental professional to temporarily repair a broken tooth and cover any exposed dentinal tubules that allow for access to nerve(s) that may be causing the person pain until the person can receive more permanent care from a dental or medical professional. A person with a broken or damaged tooth or teeth with or without an exposed dentinal tubule(s) may experience pain when a tooth breaks or a crown is broken on a previously repaired tooth. The person with a damaged tooth or teeth may also not be experiencing pain but simply want to yield an aesthetically pleasing appearance during the aforementioned interval or create a smooth surface on the tooth until further, more permanent dental care can be obtained. The temporary tooth repair compositions of the present disclosure are also able to be used to smooth out rough surfaces on a damaged tooth that may not cause pain but are felt by the person with the tooth or teeth with a rough surface or surfaces thereon.

The dental compositions, which are typically dental compositions for (a) treating sensitive teeth or delivering an active ingredient to a tooth exterior or exposed interior surface and/or (b) a temporary tooth repair compositions 10 of the present disclosure employ an uncured (uncrosslinked) silicone high consistency rubber base and one or more pigments acceptable for the buccal cavity, typically metal oxide pigments to match the color of the temporary tooth repair composition with the color of a typical natural tooth or may be color matched to the particular tooth color of the wearer as well by selecting an appropriate tint of white color. Most often the white color is a Vita Shade Range of A2-D2. The uncured (uncrosslinked) silicone high consistency rubber base employed is safe for the oral environment, more pliable and is finger pliable and shapeable than previously known compositions. The dental compositions of the present disclosure are comfortable to wear on the tooth or teeth as a temporary tooth repair composition, and has superior tensile strength. Additionally, the uncured (uncrosslinked) silicone high consistency rubber base employed is more than 18 times more pliable compared to traditional orthodontic relief wax, based on tensile testing per ASTM D412 guidance. Additionally, the uncured (uncrosslinked) silicone high consistency rubber base employed is more than 16 times more transmitting of visible light compared to traditional orthodontic relief wax, based on testing performed using a dual-beam Hitachi U-2910 UV-Vis spectrometer, making it a clearer base material for subsequent pigmentation to achieve desired tooth color(s).

As shown in the figures, when used as the temporary tooth repair composition, the dental compositions 10 of the present disclosure are easily placed into engagement with a damaged tooth (See FIG. 1A) and may be molded in place by a layperson/user (in situ) with just fingers or with fingers and the opposing tooth above or below the damaged tooth to achieve a tooth shaped facsimile (See FIG. 1B) and results in the appearance of a complete tooth where the damaged tooth portion is missing from the tooth being chipped (See FIG. 1C). No applicator tool or other tool is necessary for use of the dental compositions of the present disclosure. The dental compositions of the present disclosure typically are tooth colored and not cement based, which avoids the difficult removal of hardened material. They are also non-toxic and non-allergenic, adhere within seconds, typically within 10 seconds, 8 seconds or 5 seconds of finger pressure being applied to the composition when placed on the tooth with the adhesive containing surface on the tooth. The compositions of the present disclosure also stay in place for many hours, typically at least 4-8 hours, but up to 24 hours or even as long as 48 hours while in use.

Typically, as shown in FIGS. 1A-1C, the temporary tooth repair composition 10 creates a temporary tooth having generally the same look and appearance of an undamaged tooth and is engaged with a damaged surface 14 of a tooth or conceivably teeth. The compositions of the present disclosure may also be used to temporarily fill a missing filling that has fallen out of a cavity that may or may not expose a dentinal tubule or have accompanying pain because of the exposed tooth tissue being pressure or temperature or airflow sensitive. The dental compositions may also be used to temporarily smooth a chipped or jagged tooth that may irritate the tongue. The compositions of the present disclosure also may be used to adhere a crown or cap that has fallen off the tooth it was placed upon or as a complete temporary replacement for the cap/crown. In the case of the composition as a way to engage the cap/crown to the tooth it has fallen away from, the cap or crown is dry and a non-adhesive side of the dental composition of the present disclosure pushed into the bottom/tooth facing surface of the crown. The dry interior of the crown adheres to a non-adhesive containing/non-powder coated side of the composition pushed into engagement with the crown by the user. Next, an adhesive side/powder coated side of the composition of the present disclosure that remains exposed may be placed onto the wet portion of the tooth that remains after the crown fell off and the powder coated adhesive side adheres the composition and crown to the exposed tooth surface. No drying of the tooth surface that is exposed after the crown falls off, which can be severely painful, is necessary and may be avoided as a step entirely. The dental compositions of the present disclosure provide virtually instant pain relief by covering exposed dentinal tubules and sensitive tissues of the broken tooth or lost cap or filling (the silicone material provides an occlusive covering). The compositions of the present disclosure, as discussed herein are easy to apply and unlike prior cement composition set within seconds and not hours as is typical with traditionally used cement-based compositions. The dental compositions of the present disclosure are also typically tooth colored to repair and hide the repaired damaged tooth from visual attention from third parties. The compositions also typically have no bad taste, which is an often complained about effect of the cement-based tooth repair compositions. Also, significantly, the compositions of the present disclosure can be adhered quickly and one does not have to wait hours to eat or drink, but instead can immediately do so after the composition is applied. Also, the compositions of the present disclosure are non-toxic if swallowed and latex free, and they do not shed pieces that temporary cements often do. The compositions of the present disclosure are also packaged in hygienic single use packaging and require no special tools for application.

The devices/compositions of the present disclosure are not cured, but are purposefully finger pliable without the use of tools and shaped with fingers and/or optionally with the use of small implements such as a shaping stick or applicator, which can be made from wood, plastic or metal. The devices of the present disclosure typically yield one or more, but typically all of the following novel results:

(1) The devices are not cement based and are easily moldable and shapeable into a satisfactory tooth shape by both trained professional orthodontic staff and by untrained patients.

(2) The devices stay in place for extended period of time, typically at least about 4 hours, more typically at least 8 hours and most typically at least 12 hours after the 10 seconds or less of finger pressure is applied to adhere the composition to the tooth or teeth, typically a single tooth.

(3) The devices of the present disclosure do not "cure". Unlike the case of the cement-based materials, the dental compositions of the present disclosure do not need to cure prior to eating or drinking. More significantly, if there is any error whatsoever, since the systems previously employed are cured, it is hard to redo the process. In that case, the cement would need to be removed, which is very difficult and the entire process repeated, a fact acknowledged in the explicit instructions of the prior used products, which requires the process to start over and is why the procedure using cement is best done by an experienced professional. The material of the present disclosure typically never cures during the period of time the dental composition is in use and more typically never cures, giving an opportunity for an infinite number of corrections to the shaped, if necessary, over any period of time to get the shape right.

Figure 2:
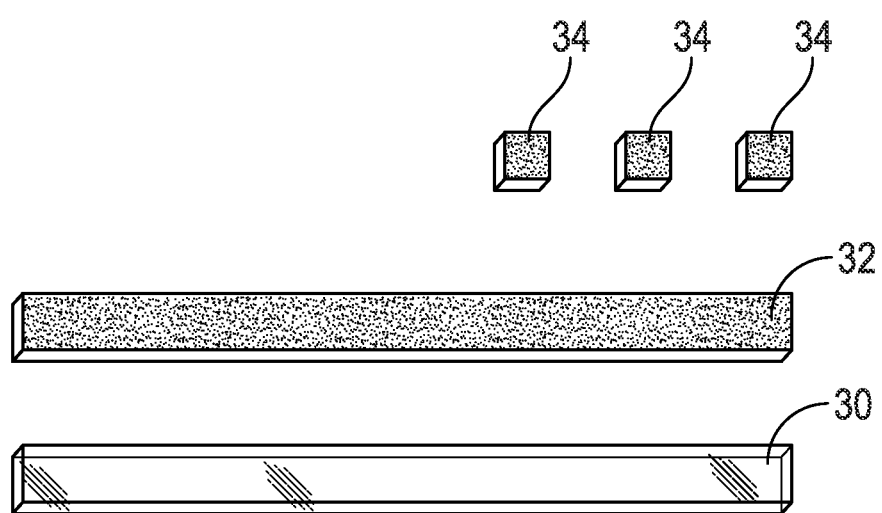
FIG. 2 is a perspective view of the following: a tooth repair composition that includes an uncoated, uncured (uncrosslinked) silicone high consistency rubber base that forms the base material of the tooth repair composition in strip form; a tooth repair composition that includes an uncoated, uncured (uncrosslinked) silicone high consistency rubber base material in strip form and coated with the dry powder adhesive composition used to adhere the tooth repair composition to the tooth surface; and the tooth repair composition that includes the uncured (uncrosslinked) silicone high consistency rubber base coated with a dry adhesive and cut in a cuboid shape to be applied to a single tooth.

As shown in FIG. 2, the material of the present disclosure the uncured (uncrosslinked) silicone high consistency rubber (HCR) base material 30, is coated on at least one, but typically not all and most typically one side of the cuboid-shaped uncured (uncrosslinked) silicone high consistency rubber (HCR) base material 30. The material is extruded in elongated bars 32 of material and subsequently coated thereon with dry powder adhesive. The bars of material are typically produced in a continuous process and cut into cuboids 34, often cubes prior to final packaging. The uncured (uncrosslinked) silicone high consistency rubber base material may include one or more colorants, typically metal oxide(s) to enable the dental compositions to more accurately match the color of the tooth or teeth of the wearer, which is typically a person but could be any animal (typically a mammal) with teeth.

Uncured (uncrosslinked) silicone high consistency rubber (HCR) base material is a blend of one or more silicones with untreated and/or treated silica filler. The uncured (uncrosslinked) silicone high consistency rubber base material incorporates proprietary silicones, proprietary amounts of silica filler and proprietary treated silica filler with proprietary material characteristics. In the industry, this information is kept a trade secret. An "uncured (uncrosslinked) silicone high consistency rubber base material" is a known category of silicone materials to chemists familiar with silicone polymers and/or silicone materials. Regarding the uncured (uncrosslinked) silicone HCR base material, many companies market uncured (uncrosslinked) silicone HCR base that could be used to prepare composites of the present disclosure, including but not limited to: Wacker ELASTOSIL® R PLUS 4000/50; Wacker ELASTOSIL® R 401/50 S; Wacker ELASTOSIL® R PLUS 4305/70; Wacker ELASTOSIL® R PLUS 4305/60; Wacker ELASTOSIL® R plus 4305/80; Wacker ELASTOSIL® R 401/80S; Nusil MED-2174; Nusil MED-4174; Hoshine HS-5253 50; DuPont Liveo Q7-4535 Medical Grade ETR Elastomer; DuPont Liveo Q7-4550 Medical Grade ETR Elastomer; DuPont Liveo Class VI Elastomers, and DuPont Liveo Q7-4565 Medical Grade ETR Elastomer. Suitable base material may also be prepared with high viscosity polydimethylsiloxane, and/or vinyl-functionalized polydimethylsiloxane, and/or silanol-functionalized polydimethylsiloxane, and/or Si—H functional silicone combined with fumed silica or trimethylsilylated silica filler. An additional class of suitable pliable materials are hydrocarbon-based waxes such as paraffin wax, bees wax, and other waxes traditionally used in the buccal cavity.

Regarding the metal oxide pigments used to obtain a color match of the silicone HCR base material to one of the VITA Classical Shade Guide colors, many companies market food grade metal oxide pigments that could be used to prepare the inventive dental material, including but not limited to, white titanium dioxide, brown iron oxide blend, and yellow iron oxide from Sensient Pharmaceutical. In the case of the compositions of the present disclosure, it is significant that through the proper combination of pigments, it is possible to obtain an uncured dental material in any of the 16 VITA shades. The VITA shades are one universal way to determine the color of a human tooth. The VITA classical A1-D4 shade guide serves to accurately determine tooth shade. The arrangement of the shades in the VITA classical family of shades is as follows: A1-A4 (reddish-brownish); B1-B4 (reddish-yellowish); C1-C4 (greyish shades); and D2-D4 (reddish-grey).

Additionally, a variety of immediate and time released flavorants such as mint flavorants, cinnamon or cinnamon flavorants, citrus flavors may also be employed. Time released flavorants are particularly effective when the dental composition is worn for many hours or days and up to about 2 weeks. Having a fresher taste is advantageous. Additionally, the dental compositions of the present disclosure may include one or more preservatives to limit bacterial growth. In particular, the composition may include, but are not limited to any one or a plurality of the following: benzoic acid and salts thereof, sorbic acid and salts thereof, and parabens. Moreover, the components applied to the exterior surface(s) of the dental compositions of the present disclosure may optionally include an analgesic (for example, benzocaine) or antibacterial composition or any dry powder, water soluble active ingredient appropriate for delivery to the buccal cavity, including enamel strengthening ingredients such as sodium fluoride, stannous fluoride, calcium salts, and phosphate salts, and hypersensitivity desensitization ingredients such as potassium nitrate, strontium chloride, strontium acetate, stannous fluoride, dipotassium oxalate, and calcium salts (with or without arginine). The dental compositions of the present disclosure are often used after damage to a tooth (including any damage to the enamel which exposes dentinal tubules) or other mouth injury occurs. Employing one or more analgesic and/or one or more antibacterial composition and/or any enamel strengthening ingredient and/or any hypersensitivity desensitization ingredient such as those discussed herein may help with the injury site pain and may help prevent infection at the site as well. The analgesic releases over time when blended with the dry adhesive and other components of the coating composition applied to the surface of the uncured (uncrosslinked) high consistency rubber base material. Exemplary analgesics that may be used alone or in combination in the dental compositions of the present disclosure include: benzocaine; an NSAID such as ibuprofen; acetaminophen; and acetyl salicylic acid. Exemplary antibiotics that may be employed alone or in combination in dental compositions of the present disclosure include, but are not limited to, erythromycin, clarithromycin and azithromycin. Some of the distinct advantages of the devices of the present disclosure as a delivery method of any of the above active ingredients over other delivery methods of the above active ingredients such as toothpastes, mouth washes/rinses, chewing gums and lozenges are: (1) The inventive device targets/delivers the active ingredient(s) to the effected tooth as opposed to the entire buccal cavity; (2) the occlusive and hydrophobic nature of the silicone portion of the inventive device that delivers the active ingredient(s) to the thin film of saliva that coats the tooth and prevents their dissolution and dilution by additional saliva thereby maintaining an efficacious concentration at the tooth such that they perform their function in reduced time (functions such as deadening nerves and occluding dentinal tubules via precipitation), and (3) in the case of hypersensitivity, offers instant occlusion of exposed dentinal tubules while worn to provide instant relief from hypersensitivity, and extended occlusion of exposed dentinal tubules and extended relief from hypersensitivity when removed. The use of the combination of stannous fluoride, which creates occlusion of exposed dentinal tubules and provides relief from hypersensitivity by physically blocking the exposed dentinal tubules, and potassium nitrate, which provides relief from hypersensitivity by deadening the nerves, together, as discussed above, are often used in the context of the compositions of the present disclosure. Due to the fact that the devices of the present disclosure prevent dilution by saliva of the components/active ingredients, it has been surprisingly discovered that less of these components/active ingredients than would typically be needed to be effect may be used while still maintaining efficacy of the treatment of exposed dentinal tubules. Moreover, unlike toothpastes marketed for sensitive teeth or any aqueous or glycerin based composition, the compositions of the present disclosure typically include both potassium nitrate and stannous fluoride over the entire shelf life of the product. The potassium nitrate and stannous fluoride, when included in the coating compositions of the present disclosure are typically in stable, solid form, typically a dry powder form without any added water. These two components cannot be combined in a toothpaste marketed for sensitive teeth because they react with one another to shorten shelf life to unacceptable levels. In toothpaste marketed for sensitive teeth, potassium nitrate individually and stannous fluoride individually are used in an amount of 0.454% by weight volume of the toothpaste. In the context of the compositions of the present disclosure, the two components are typically combined and stable and present in an amount of up to about 5 percent by weight of the coating composition, more typically in an amount of from about 0.01 by weight to about 5 percent by weight of the coating compositions of the present disclosure. However, it has been surprisingly discovered that not only can these two chemicals that decrease tooth sensitivity in different ways be used, but they can be used in drastically lower amounts as well and be more effective due to their extended application period directly to the surface of the tooth and the shielding from dilution by additional saliva from the buccal cavity during use. Accordingly, the compositions of the present disclosure may use and most typically do use less of each of these components and, while the components may be used individually, they are typically both employed. Most typically both the stannous fluoride and the potassium nitrate are present in an amount of about 0.15 percent by weight to about 0.5 by weight percent of the coating compositions of the present disclosure.

According to an aspect of the present disclosure, the dental composition of the present disclosure was prepared by combining metal oxide pigment(s) with uncured (uncrosslinked) silicone HCR base (DUPONT® LIVEO®. Q7-4550) on a two-roll mill. Other mixing technologies that could be used include, but are not limited to, a sigma blade ("Z-blade") mixer and a double planetary mixer equipped with high viscosity blades or a SPEEDMIXER™, which is a double rotation of the mixing cup that is sometimes referred to as a dual asymmetric centrifuge. The combination of centrifugal forces acting on different levels in such a device enables very rapid mixing. Batches ranging up to 25 pounds were prepared using a two-roll mill. The following example illustrates the pigment compositions required to achieve inventive dental material of VITA™ Shade D2 as established by visual comparison to a reference and by color mapping using camera input analyzed using SHADE-WAVE™ Dental Shade Matching Software (shadewave.com).

Example dental composition VITA™ Shade D2 below.

| Example | % Q7-4550 | % titanium dioxide | % brown iron oxide blend | % yellow iron oxide |
|---|---|---|---|---|
| VITA ™ Shade D2 | 99.964 | 0.0312 | 0.0012 | 0.0039 |

The amount of uncured, uncrosslinked silicone high consistency rubber base (Q7-4550, for example) typically ranges in amounts by weight of from about 99.90 to about 99.99 weight percent of the dental composition, more typically from about 99.92 to about 99.98 weight percent of the dental composition. The amount of titanium dioxide typically ranges from about 0.020 to about 0.055 weight percent, more typically from about 0.030 to about 0.045 weight percent of the dental composition. The compositions of the present disclosure typically include one or a plurality of different iron oxides to adjust the color of the dental to any appropriate VITA shade to match the person's other natural or artificial teeth color. For example, a first iron oxide and a second iron oxide may be employed. A third iron oxide or any number of subsequent iron oxides may be employed as well. Typically, the iron oxides employed are brown iron oxide and yellow iron oxide. The amount of brown iron oxide blend typically ranges from about 0.0005 to about 0.015, more typically from about 0.001 to about 0.010 weight percent of the dental composition. The amount of yellow iron oxide typically ranges from about 0.002 to about 0.006, more typically from about 0.0030 to about 0.0050 weight percent of the dental composition. The resulting dental material may be rolled into sheets or extruded into rods or into pre-cut small pieces as possible modes of marketing. Red iron oxide pigment may also be used in combination with the above pigments to obtain a VITA Shade match. The materials are typically mixed together thoroughly at room temperature, a temperature of from about 65 degrees Fahrenheit to about 80 degrees Fahrenheit, but the temperature of the mixing is not presently believed to be critical.

An additional benefit of the dental compositions of the present disclosure is the ability to adjust opacity from being completely opaque to translucent depending on the amount of titanium dioxide pigment and the thickness of the inventive dental material. For example, the above example is opaque at a thickness of 3 mm, mostly opaque at a thickness of 2.5 mm, and somewhat translucent at a thickness of 2 mm or less. Natural teeth often progress from opaque to somewhat translucent as one progresses from the cervical to the incisal edge. The inventive dental material allows one to mimic this behavior by varying the amount of titanium dioxide pigment in the material and/or the thickness of the material once placed into engagement with the tooth or teeth.

The dental compositions of the present disclosure typically have the dry adhesive gravity deposited, dusted, sprayed or otherwise applied to one surface therefore. Applying, which is typically done by gravity depositing the dry powdered hydrophilic polymeric substance and any other dry silicone adherable material thereto onto the malleable hydrophobic material, and may be accompanied by may be accomplished by a variety of mechanical means, either separately or in combination, and include a press, a roller, rods, a blade, all of which make contact with the surface of the malleable hydrophobic material to which the powdered hydrophilic polymeric substance has been deposited. Removing loose dry powdered hydrophilic substance that does not adhere to or is not impregnated into the surface of the malleable hydrophobic material may be accomplished by shaking, brushing, air pressure, an ion air knife, or vacuum. Alternatively, upon contact of the dry powdered hydrophilic substance with one or more surfaces of the malleable hydrophobic material, no rubbing or pushing of the dry powdered hydrophilic substance may be done, and no removal of loose dry powdered hydrophilic substance may be done, and the dental composition used "as is".

Suitable malleable hydrophobic materials that may be used in the context of the present disclosure include, but are not limited to: Orthodontic relief Wax (a product consisting of one or more hydrocarbon-based waxes that may also include inorganic and/or organic fillers); uncured (uncrosslinked) silicone high consistency rubber (HCR) base material, which as discussed above is a blend of one or more silicones with untreated and/or treated silica filler, or any hydrophobic water insoluble solid material that is malleable at 37° C. or lower and safe for the human oral environment. The uncured (uncrosslinked) silicone high consistency rubber base material incorporates proprietary silicones, proprietary amounts of silica filler or treated silica filler possessing proprietary material characteristics. In the industry, this information is kept a trade secret. An "uncured (uncrosslinked) silicone high consistency rubber base material" is a known category of silicone materials to chemists familiar with silicone polymers and/or silicone materials. Regarding the uncured (uncrosslinked) silicone HCR base material, many companies market uncured (uncrosslinked) silicone high consistency rubber base that could be used for inventions of the present disclosure. These include but are not limited to: Wacker ELASTOSIL® R PLUS 4000/50; Wacker ELASTOSIL® R 401/50 S; Wacker ELASTOSIL® R PLUS 4305/70; Wacker ELASTOSIL® R PLUS 4305/60; Wacker ELASTOSIL® R plus 4305/80; Wacker ELASTOSIL® R 401/80 S; NUSIL™ MED-2174; NUSIL™ MED-4174; Dow Corning SILASTIC® Q7-4535 Medical Grade ETR Elastomer; DUPONT® LIVEO® Q7-4550 Medical Grade ETR Elastomer; DUPONT® LIVEO® Q7-4565 Medical Grade ETR Elastomer, DUPONT® LIVEO® Class VI Elastomers, and HOSHINE® HS-1552PT High Transparency Extrusion Silicone Rubber. The malleable hydrophobic material may be extruded or otherwise formed by shaping the material. Other ways of forming the base, malleable, hydrophobic material into a shaped base include, but are not limited to, using a mechanical flat press or a roller press to produce flat sheets that are then coated with the dry powdered hydrophilic polymeric substance(s) and cut into pieces, or pressing the base, malleable, hydrophobic material into a mold, then opening the mold and removing the shaped pieces, which would thereafter be coated with the dry powdered hydrophilic polymeric substance(s) and optionally cut into smaller pieces or shaped, or the powdered hydrophilic polymeric substance(s) could be directly deposited (dusted) onto the mold surfaces as a mold release agent, ending up incorporated onto the surface of the molded piece.

Suitable dry powdered hydrophilic polymeric substances are those that can serve as moisture activated pressure sensitive adhesives and absorb water and are substantially soluble in water. These include, but are not limited to, any material from a list comprising: polyvinylpyrrolidones (PVPs), polyoxazolines, polyethylene glycols, starches, polyacrylic acids, carbomers, polyvinyl alcohols, polyvinyl acetates, cellulose derivatives, polysaccharides (such as xanthan gum, pectin, guar gum, starches, cellulose ethers, chitosan derivatives), polyacrylamides, N-vinyl caprolactam polymers, and copolymers of methyl vinyl ether and maleic anhydride (PVM/MA), and other water-soluble polymeric adhesives or blends of any of the above or other water-soluble polymeric adhesives, including, but not limited to, TICALOSE® CMC 15 Fine, TICALOID® 750, SALADIZER® 210, TICAGEL® Gellan HS, TICA-ALGIN® 400, METHOCEL® HPMC K100M, Locust Bean Gum POR/A2, METHOCEL® K100M Premium HPMC DC2, ASHLAND™ NATROSOL™ 250HHW Pharm, INGREDION® pre-hydrated Pectin 1400, LUBRIZOL® CARBOPOL® 971P NF Polymer, LUBRIZOL® CARBOPOL® 974P NF Polymer, LUBRIZOL® NOVEON® AA-1 Polycarbophil USP, and mixtures of two or more of any of the above.

The water-soluble polymeric adhesive(s) are safe for use in the buccal cavity of a human. One particular polyvinylpyrrolidone that may be used is PLASDONE® K-29/32 polymer, which is a stable, water-soluble polyvinylpyrrolidone that meets U.S., European and Japanese pharmacopoeia specifications for povidone. One particular polysaccharide that has been found to be effective is xanthan gum as the only or the majority dry powder adhesive of the coating powder portion of the dental compositions of the present application. It is currently believed that pre-hydrated guar gum powder that has been further hydrated beyond the level when commercial purchased performs surprisingly better as an adhesive powder than other dry powders used whereas the use of commercially available pre-hydrated guar gum 8/22 powder from INGREDION®, for example, does not work as well. The level of hydration is believed to be a surprisingly significant factor in the implementation of guar gum as a dry adhesive powder. The use of guar gum as a superior dry adhesive appears to be dependent on the hydration level of the guar gum prior to its application as a "dry" ingredient. In the context of the present application a "dry" ingredient does not mean that the component is devoid of any water molecules, but rather that it is capable of being dusted onto a surface of the extruded substrate, which is typically the uncured (uncrosslinked) high consistency silicon rubber. In the context of the pre-hydrated guar gum 8/22 powder product from INGREDION® the moisture level of the purchased/supplied product is reported to be from 0% to 12%. It is presently believed the higher levels of hydration than 12% while maintaining a dry powder dustable physical form surprisingly produces superior adhesiveness qualities. Xanthan gum, for example, has a viscosity of 3300 cP in a 1% aqueous gel solution whereas a hydrated above 12% guar gum was tested to have a viscosity of 5300 cP in a 1% aqueous gel solution.

The adhesiveness of various adhesive powders has also been tested. To conduct these tests, first, Dupont Liveo Q7-4550 high consistency silicone base was extruded through a 3 mm×6 mm rectangular die using a ram extruder and cut into 6 mm lengths (herein referred to as "samples") for trials. The samples were coated with adhesive polymer powder via rolling by hand in the powder and then transferred with forceps into a clean plastic weigh boat and gently shaken for five seconds to remove excess powder. Samples were then placed on the end of a rotating (50 rpm) shaft while a fine mist of water was applied to the sample for 20 seconds (mist produced using pressurized water and a Spray Systems 1/4LNN-SS1 spray nozzle). The wetted sample was removed from the rotating spindle via forceps and placed on a texture analyzer stage (lower test surface of a Brookfield CT3 texture Analyzer). The upper test surface was a translucent 25.4 mm diameter acrylic cylindrical probe having a completely smooth surface connected to a 25,000 gm load cell. A compression test cycle was chosen to closely approximate the pressing of a sample onto a tooth, with a trigger load set-point being reached upon contact of the upper test surface with the sample. The instrument then continued to flatten the sample until a target distance set point was reached. After a set hold time of 5 seconds once the sample was flattened, the upper probe was pulled away from the sample at a rate of 0.3 mm/s. Adhesiveness (mJ) was measured and is the total amount of work done during the process of pulling the upper probe away from the flattened sample. Polysaccharides were demonstrated to be the best dry powders to be used as adhesives in the context of the dental compositions of the present disclosure; however, this is not the only factor to be considered. The adhesive tests showed the following:

| Adhesive Powder | Adhesiveness (Work to Remove in mJ) |
| --- | --- |
| Guar Gum | 1.18 |
| POLIGRIP® | 1.02 |
| Xanthan Gum | 0.92 |
| Polyvinylpyrrolidone (PVP) | 0.53 |

POLYGRIP® is an over the counter adhesive that consists of two ingredients: carboxymethyl cellulose (CMC) and polyvinyl methyl ether/maleic acid (PVM/MA).

The average duration of adherence with different adhesive powders was tested by first applying by shaking the dust of the adhesive powder to be tested onto the surface of the base material, the uncured (uncrosslinked) silicon base. Next, the excess powder was shaken off, and the devices were applied to wet with saliva second bicuspids (second premolars) upper teeth #4 and #13 and worn overnight. Test results are averages of multiple measurements and indicate how long the device stayed attached until it fell off. Longer durations than those shown in the table are achieved and depend on which teeth are used for testing.

| Adhesive | Average Duration |
| --- | --- |
| Poligrip Super Denture Adhesive Powder | 2.75 hr (max 3 hr) |
| Vanderbilt Minerals VanzanNF xanthan Gum | 3.6 hr (max 4 hr) |
| Ingredion pre-hydrated GuarNT 8/22 having additional hydration such that it is above 12% water but remaining a dust/powder for application | 7.2 hr (max 9 hr) |

Another aspect used to evaluate the effectiveness of different adhesive powders is adhesive tack. Tack is a measure of how quickly an adhesive bond is formed when two surfaces are brought together. The faster two surfaces bond, the higher the tack. Good adhesive tack is important for the dental composition of the present disclosure as it helps the devices to grab hold and keep from sliding off during application. The compositions of the present disclosure improve tack at least two ways. First, a polysaccharide gum such has xanthan gum and pre-hydrated guar gum with extra hydration above 12% may be employed. Second, the size of the adhesive powder particles is believed to be important. The smaller particles of the powdered adhesive also appear to be a factor and the smaller particles are believed to work better than others due to their higher surface area and ability to wet and form sticky gel faster, thereby providing good tack. Smaller particles can however also get pushed (buried) into the soft silicone upon application of the device to the tooth, hiding them from saliva, which is negative impact for tack. The pre-hydrated guar gum having a hydration in excess of 12% water is believed to surprisingly have small particle size, but the particles clump together to make large clusters, which resist being buried and inaccessible to activation by saliva and use by the composition to adhere to a surface of the tooth or teeth.

Additionally, as discussed above and herein, one or more dry powdered flavor substances may be added to the hydrophilic polymeric substances mentioned above to yield a flavor sensation to those using the devices upon application to teeth that are wet with saliva. In addition, water soluble (to any extent) compounds that produce a variety of benefits to tooth enamel and oral health in general can be included and mixed with the dry powdered hydrophilic polymeric substance and be delivered in an effective amount and manner over a treatment effective period of time. One or more such compounds may be used. While not typically used in the temporary tooth repair dental compositions of the present disclosure used to repair lost fillings, disengaged caps or crowns and/or chipped or broken teeth, some of the treatment or benefit inducing compounds that can be included into in a mixture with the dry powdered hydrophilic substance(s) to form the mixture that is applied to a surface of the malleable hydrophobic material include, but are not limited to, the following: sodium fluoride, stannous fluoride, acidulated phosphate fluoride, sodium monofluorophosphate, calcium sulfate, calcium acetate, calcium lactate (with or without addition of xylitol, the combination remineralizes tooth enamel), calcium phosphate, amorphous calcium phosphate complexed with casein phosphopeptides, tricalcium phosphate that has been mechanochemical ball milled with fumaric acid, calcium sulfate, sodium phosphate, potassium phosphate, dipotassium phosphate, and others. Calcium salts and phosphate salts with or without fluoride or carbonate salts may be used. Materials such as calcium chloride, sodium phosphate and sodium fluoride may be placed into non-aqueous mediums and, when they come into contact with saliva, for example, are then re-precipitated as amorphous calcium phosphate, amorphous calcium phosphate fluoride, amorphous calcium carbonate phosphate or amorphous calcium carbonate phosphate fluoride for remineralization of the teeth. The remineralization is further aided by the extended time the composite with the treatment material/components contained therein are applied to the teeth in the context of the present disclosure and their positioning directly around, adjacent and over the braces, which are particular locations where demineralization often occurs when braces are worn. The area around the orthodontic device is particularly treated. In addition, any of the above combination of benefit inducing compounds that lead to precipitate formation in exposed dentinal tubules may be employed for treatment of dentin hypersensitivity.

In particular, it has been discovered that compounds used to reduce sensitivity of teeth may be applied to the enamel of the teeth through the application of a dental composition of the present disclosure. When the dental compositions of the present disclosure are used to help reduce teeth sensitivity, the dental compositions may be applied to damaged or undamaged, but nevertheless sensitive teeth. One or a plurality of different tuble blocking or occluding agents may be employed as component of the dry powdered ingredients. If used, the tooth or teeth desensitizing agents that block or occlude exposed dentin tubules may be blended with the dry powder adhesive as well as any other optional dry components to be applied to the surface of the tooth or teeth to form a homogenous blend of dry powder ingredients before it is applied to at least one surface of the uncured (uncrosslinked) silicon base material or other finger force malleable hydrophobic material.

The tuble blocking or occluding agent(s) that may be included include, but are not limited to: strontium salts such as strontium chloride and strontium acetate; Arginine with calcium carbonate (8% by weight calcium carbonate); calcium sodium phosphosilicate; stannous fluoride; and combinations thereof. The tuble blocking or occluding agent(s) can be used to occlude or block dentinal tubules, which prevents stimuli from causing fluid flow in the tubules of the teeth thereby preventing the nerve endings inside the tooth from being stimulated. Arginine and 8% calcium carbonate (sold under the trade name PRO-ARGIN™) PRO-ARGIN™ blocks tubules upon its application by depositing calcium- and phosphate-containing minerals within the dentinal tubules. Both arginine and calcium carbonate ($CaCO_3$) are required for this action. Arginine is found naturally in saliva. Arginine may help usher calcium to open tubules for incorporation of calcium phosphate into dentin. Calcium carbonate creates a basic environment, and calcium phosphate salts are less soluble at higher pH (more basic). The combination of high local calcium concentration at the dentin tubule at basic pH is designed to promote precipitation of calcium phosphate salts and reduce sensitivity.

Strontium acetate is another tuble blocking or occluding agent that may optionally be used in the context of the dental compositions of the present disclosure. Unlike the original strontium chloride, strontium acetate can be formulated into fluoride-containing dentifrices. Upon toothbrushing, strontium-based precipitates form to occlude dentinal tubules and build a resistant barrier over time.

Yet another tuble blocking or occluding agent that helps desensitize teeth when used in connection with the dental compositions of the present disclosure is calcium sodium phosphosilicate)(NOVAMIN®). In saliva, NOVAMIN® releases calcium and phosphate ions and raises the pH. Under these conditions, calcium phosphate salts precipitate from solution to not only block dentin tubules but also to form an insoluble calcium phosphate layer on the surface of enamel.

Additionally, one or more colorants (pigments) that are safe for use in the buccal cavity may be added to the base material to achieve a finger force malleable hydrophobic material of any color.

Conceivably, the present dry powdered hydrophilic polymeric substance(s) alone or, as discussed above, in combination with one or more of any of the above-mentioned materials, typically the water-soluble materials may be mixed or blended together into a mixture/blend, which is typically a homogenous blend, to be applied to a surface of one or a plurality of surfaces of the malleable hydrophobic materials. The dry powdered hydrophilic polymeric substance(s) adheres the overall device to a tooth and facilitates delivery of the treatment or tooth benefit material such as the teeth desensitizing agent(s) to a surface of one or more of these tooth beneficial materials onto the teeth surfaces or an individual tooth surface and used for delivery of one or more treatment compositions or compound types whether or not an orthodontic device or devices are present. Typically, an orthodontic device such as a brace will not be present however, but could be present. As with the dry powdered hydrophilic polymeric substance, typically xanthan gum, due to the water-soluble nature of the materials, they hydrate when applied to the surface of the tooth or teeth. Also, one could incorporate glycerin and PVP into the base uncured (uncrosslinked) silicone base material along with one or a plurality of tuble blocking or occluding agents to help reduced sensitivity in teeth, but it is presently believed this will be less effective since greater amounts of material would be needed to produce such a dental composition and less tuble blocking or occluding agent(s) would be brought into engagement with the surface of the tooth. Nevertheless, this may be another delivery mechanism for providing tuble blocking or occluding agent(s) into engagement with a surface or the surfaces of a tooth or teeth to reduce their sensitivity.

DuPont Liveo® Q7-4550 High Consistency Rubber Base may be extruded through a 6 mm×3 mm stainless steel die to produce mostly clear, colorless rectangular rods (See FIG. 2). These rods adhere to dry surfaces but totally non-adherent to wet (with water) surfaces. Next, xanthan gum may be applied by dusting (a process of sprinkling the dry powder xanthan gum onto the surface of the rods such that the rods have at least the upward facing surface substantially or completely covered with the dry powder component(s) of the present disclosure, in this case just the xanthan gum. Excess dry powder may optionally be removed from the surfaces of the rod by brushing it off either with a nylon brush or simply with a finger, resulting in an opaque surface appearance due to the powder coating that adhered to the rod. As shown in FIG. 2, pieces of 6 mm length were cut from the rod, resulting in 3 mm×6 mm×6 mm pieces in which the two 6 mm×6 mm faces and two of the 6 mm×3 mm faces may be coated with powdered xanthan gum. When these pieces are applied (pushed on with pressure from a dry finger) to wet teeth in such a manner that one of the coated surfaces contacted the wet teeth, the piece adhere to the wet tooth and stay on the tooth for three to eight hours, during which time food and beverages may be consumed. Additionally, the piece in contact with the dry finger will not adhere to the dry finger. Additionally, the same adhesive behavior will be observed if excess xanthan gum is not brushed off before application to the wet tooth.

Excess dry powder xanthan gum beyond what is necessary to adhere the dental composition to the tooth is typically deposited onto a textured surface of an extruded rod of base material, the xanthan gum may be rubbed into the surface with gentle pressure using a dry finger or the flat surface of a stainless-steel spatula or a smooth or textured metal roller. Excess powder may be removed from the surfaces of the rod by brushing it off either with a nylon brush or simply with a finger. The result of the application of the dry powder onto a surface of the extruded rod of base, finger malleable material is an opaque surface appearance due to the powder coating that adhered to the rod and some white spots due to xanthan gum-filled depressions on the textured surface. The opaque nature of the dry powder surface is advantageous because it readily tells a user of the dental compositions of the present disclosure which side is the adhesive or adhesive and another dry component/active ingredient containing surface.

Figure 3:
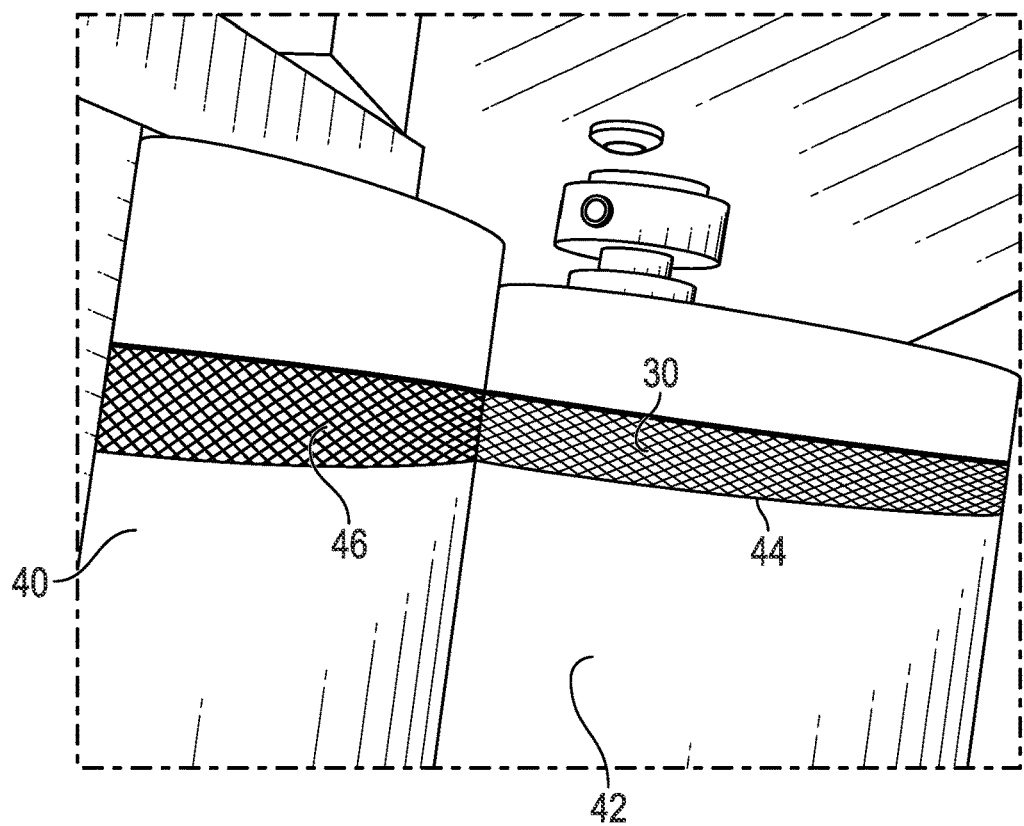
FIG. 3 is a close-up, perspective view of two rollers, one feeding the uncured (uncrosslinked) silicone high consistency rubber base material having tooth color dispersed therein and used to form the tooth repair composition and the other having a knurled or grooved or other textured surface to both optionally create indentations into the base material and also facilitate the retention of the dry powder adhesive material in engagement with the base uncured (uncrosslinked) silicone high consistency rubber base material where the entire tooth repair composition is moldable using finger pressure only and without the use of dental tools by a person other than a dental professional.
Figure 8:
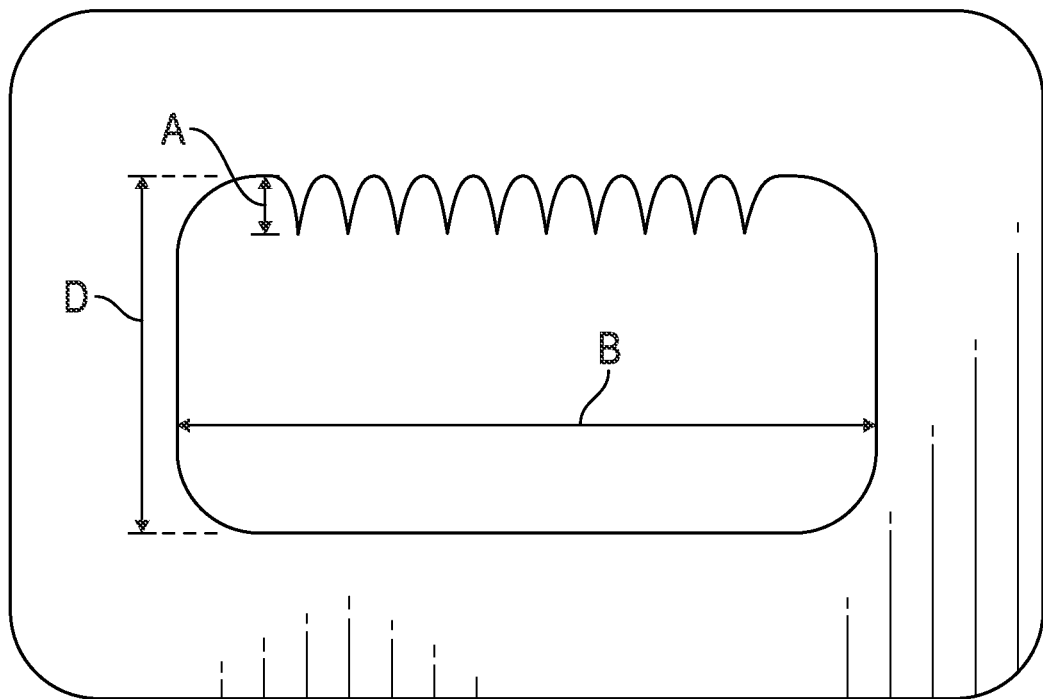
FIG. 8 is a cross-sectional view of an extrusion die opening that has a pattern that may optionally be used to cut/form microgrooves on a single surface of the base material of the present disclosure.

As shown in FIG. 3, the method of applying the dry powder adhesive material of the present disclosure may utilize a knurled or otherwise textured roller 40 and a second roller 42 that has a groove/channel 44 that receives hydrocarbon wax or silicone-based finger force malleable hydrophobic base material 30. Notably, while it may do so, the knurled or otherwise textured roller does not typically apply a texture to the extruded base material 30. The textured surface is obtained using a die during the extrusion process (see FIG. 8 and FIG. 12). Instead, the knurled or textured roller utilized the cavities in the roller to hold the dry powder adhesive material before it is applied. If a texturization is made to the base material, this texturization is done as the base material is extruded by extruding the base material through an extrusion die as shown in FIG. 8. The extrusion die has an about 6 mm×about 3 mm shape. The pattern on one surface, the surface to receive the dry powder adhesive, is a series of microgrooves producing projections (A) extending from a side of the die and having a maximum depth of about 0.02 inches, but conceivably the depth could be from about 0.4 to about 0.01 inches. The main purpose of the grooves would be to create substantially V-shaped channels within which the dry adhesive material (and optionally other dry and also typically water-soluble components) may be placed as the extruded rod passes through the overall system and the knurled or otherwise textured roller 40 and the second roller 42. Conceivably, the use of a textured roller 40 is unnecessary when the micro-grooved extruded rod of base material is employed, but typically both are utilized to ensure the dry powder adhesive is delivered into the microgrooves. As shown in at least FIG. 3, the two rollers 40, 42 are proximate one another such that the dry powder adhesive material in the textured surface on one side of the base material 30 (the optionally micro-grooved side) is delivered into engagement with the base 30 within the created textured surface 46 or on the flat unmicrogrooved surface of the extruded rod of base material 30. In FIG. 3 and other figures of this application, the textured surface, which would typically have linear (typically V-shaped) grooves consistent with the die shown in FIG. 8, is shown with the adhesive powder applied in the knurled pattern on the base material. However, the grooves typically would be present. This creates a continuous production process.

Figure 4:
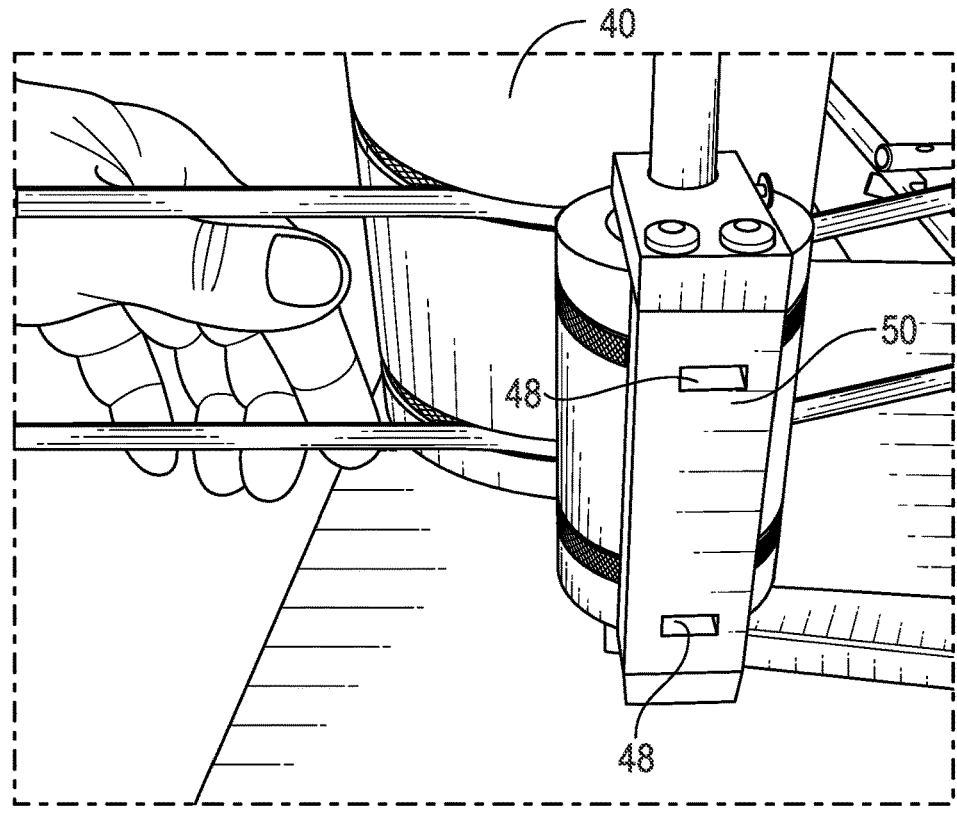
FIG. 4 is an enlarged perspective view of a system of the present disclosure employing a twin roller system to create the tooth repair composition products of the present disclosure. In particular, the dry powder feed cavity is shown in the guide above the knurled or textured roller to feed dry powder into the textured surface of the roller prior to it being mechanically forced into engagement with the uncured (uncrosslinked) silicone high consistency rubber base material having white coloring component therein to match the natural color of a person's tooth.
Figure 5:
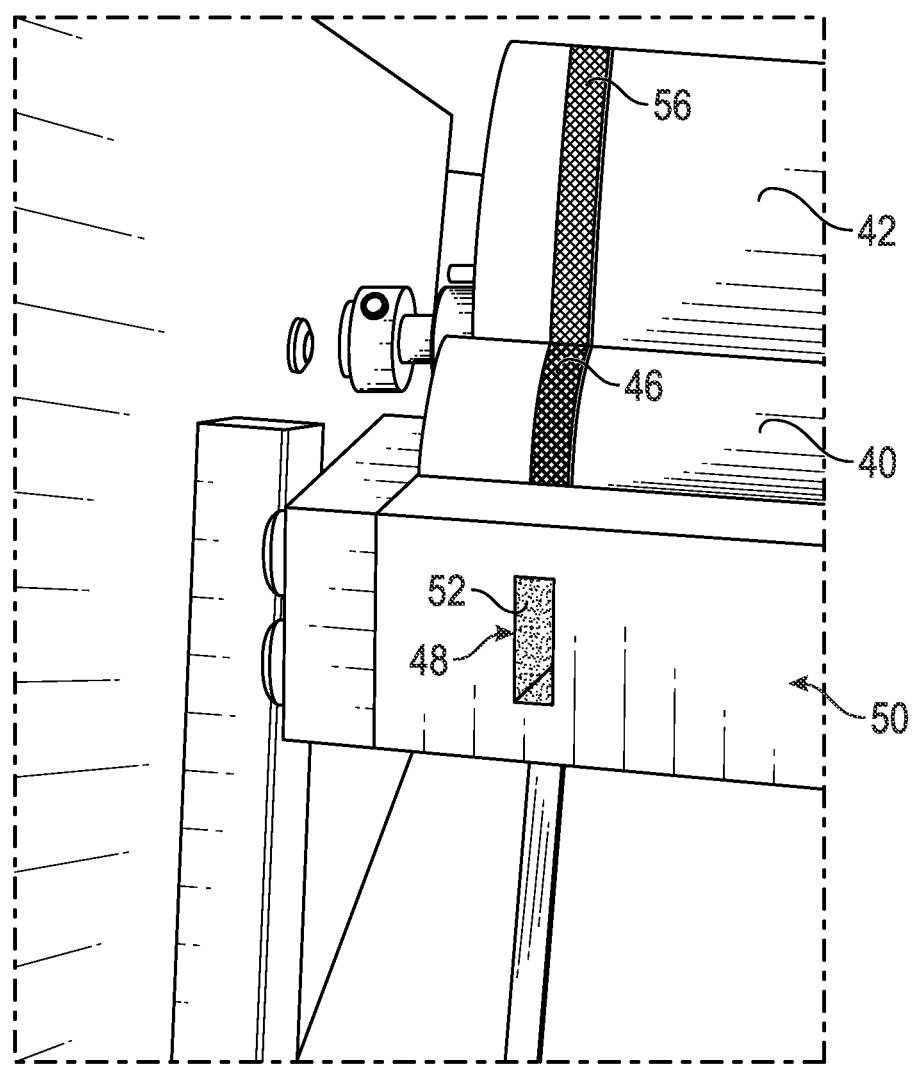
FIG. 5 is an enlarged upper perspective view of the dry powder feed cavity shown in FIG. 4, but with powder inserted therein.
Figure 6:
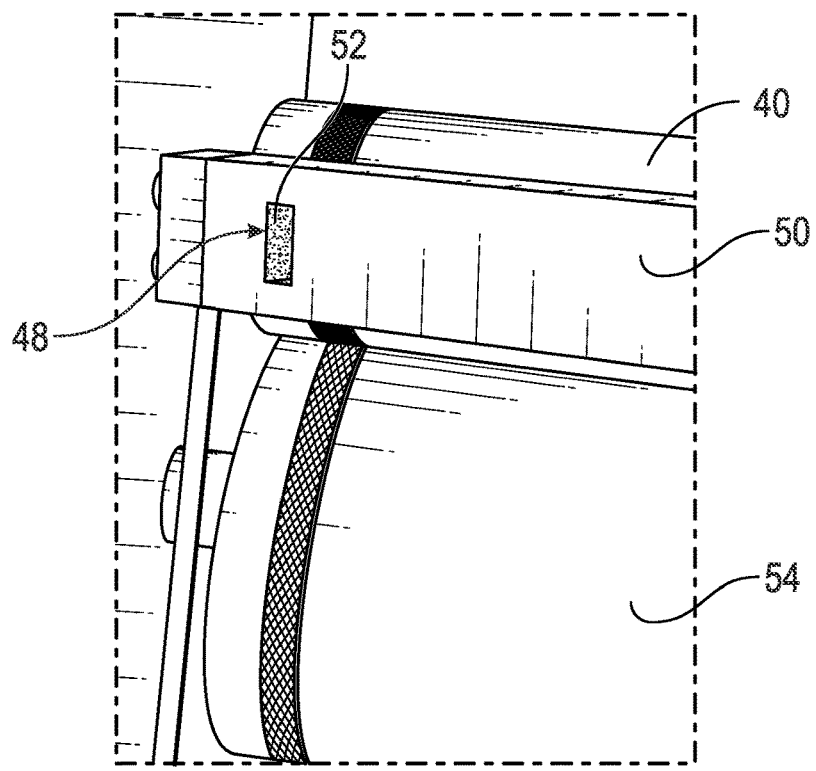
FIG. 6 is an enlarged perspective view of a roller system of the present disclosure with the rollers aligned next to one another with the dry powder feed cavity spaced above the textured surfaced roller and the base delivering roller and the textured roller adjacent laterally with one another.
Figure 7:
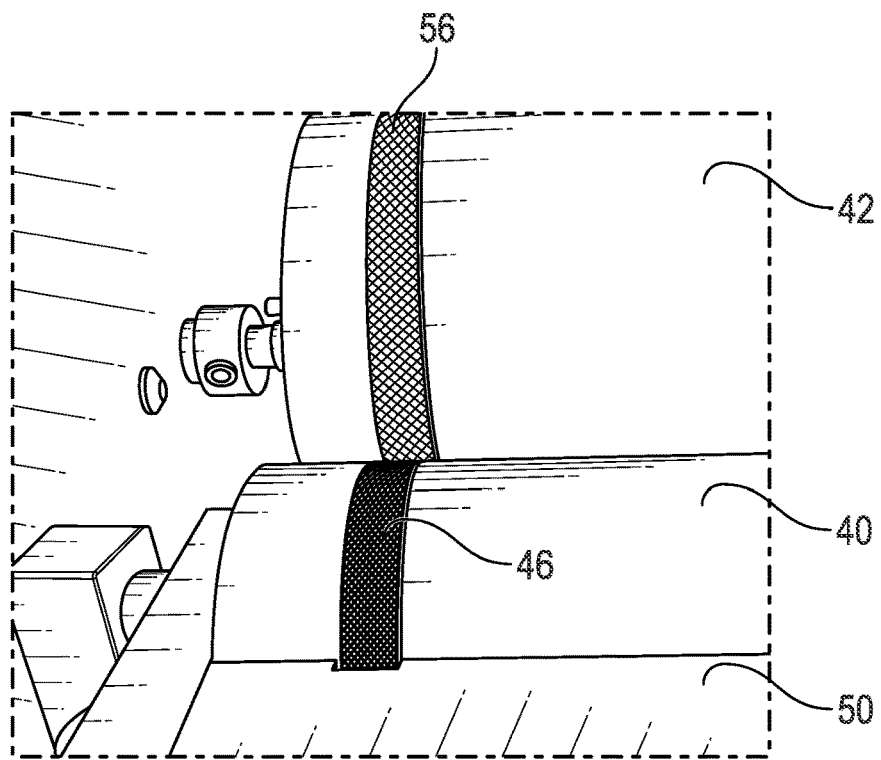
FIG. 7 is an enlarged perspective view of a system of the present disclosure with the textured roller receiving the dry powder and spaced above the tooth repair composition uncured (uncrosslinked) silicone high consistency rubber base material delivering roller.

FIG. 4 shows the process for forming the composite material of base 30 and powder engaged to a surface of the composite, but shows the system without the powder inserted into the dry powder feed cavity 48 in the powder guide bracket 50, which is spaced above the textured or knurled roller 40 such that powder is delivered to the grooves of the textured or knurled portion 46 of the roller 40. The roller 42 may be spaced below or adjacent or otherwise in a force receiving engagement with the textured roller 40. FIG. 5 shows the system with the dry powder particles 52 generally shown filled into the dry powder feed cavity 48. FIG. 6 shows the system with a third roller 54 on the feed side of the system to feed the base material 30 into the knurled or textured roller 40. The base material is shown smooth on this side of the system. FIG. 7 shows the other side of the system after the powder is applied and texturizing done to the base material to form the dry powder coated composite orthodontic protection device material 56 of the present disclosure.

FIG. 8 shows a cross-sectional view of the die of the extrusion of the present disclosure. The die forms a plurality, typically about five (5) or more, of grooves on a length of the rectangular cross-section. The die shown in FIG. 8 is one version of an extrusion die opening that is roughly 6 mm (B)×3 mm (D) that has a pattern that would be cut into it using EDM (Electric Discharge Machining) wire cutting. The die places microgrooves into the surface of the silicone rod. The microgrooves receive the hydrophilic polymeric substance(s) such as xanthan gum or PVP in powder form when it is deposited onto it. This does two things: First, the microgrooves make the surface that has been powdered more obvious to the user. Second, the grooves carry additional amounts of hydrophilic polymeric substance(s) such as xanthan gum or PVP. While not necessary for adhesion, the added amounts of the hydrophilic polymeric substance(s) facilitate greater adhesion forces to the surface of the tooth/teeth and/or a surface of a dental appliance or orthodontic device. FIG. 8 shows ten grooves, however, fewer or more grooves may be employed. Typically, ten or fewer, more typically five grooves or fewer are used.

Figure 9A:
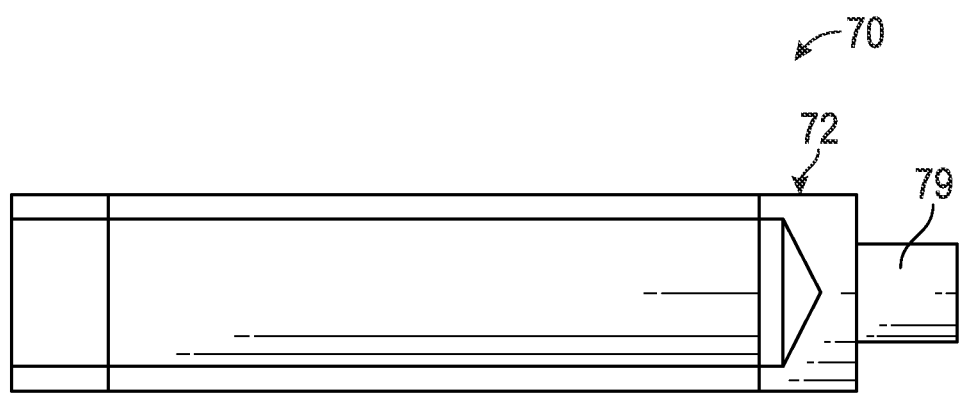
FIG. 9A is an elevated side view showing a cutout location of a urethane rod and a coaxial, swivel bar engaging peg.
Figure 9B:
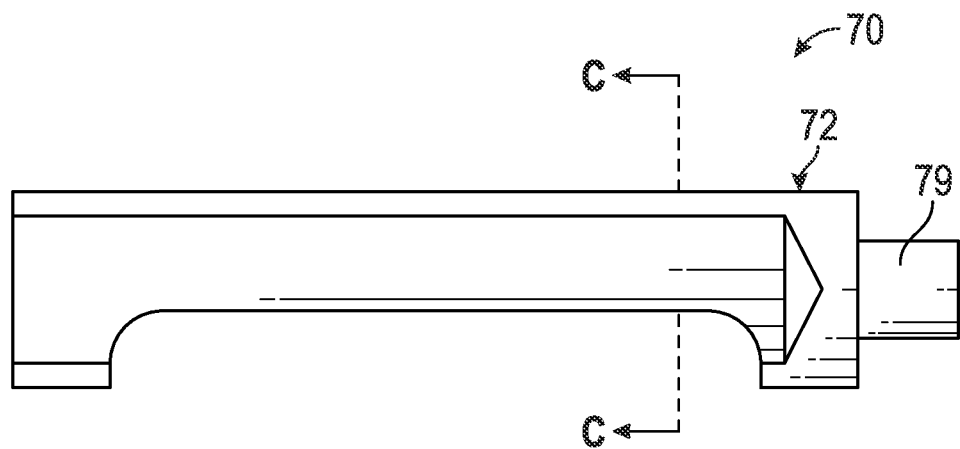
FIG. 9B is an elevated top view showing a cutout location of a urethane rod and a coaxial, swivel bar engaging peg.
Figure 9C:
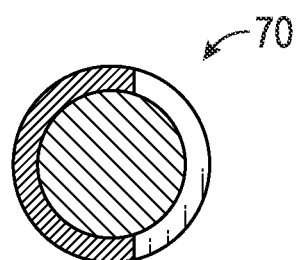
FIG. 9C is a cross-sectional view taken along line C-C in FIG. 9B.
Figure 10:
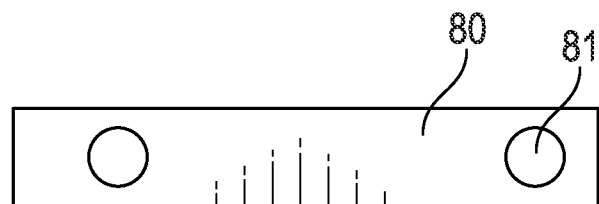
FIG. 10 is an elevated plan view of a swivel bar that holds the urethane rod holder containing a urethane rod therein and allows for adjustable or fixed amount of pressure to be applied to the adhesive and engage it to a surface of the base material.
Figure 11:
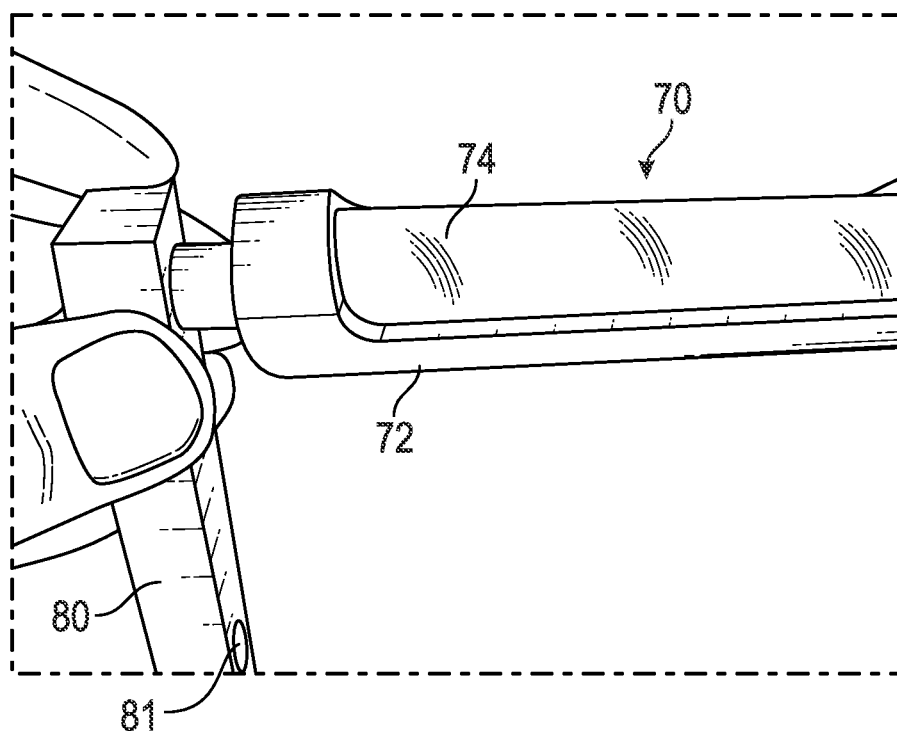
FIG. 11 is a perspective view of the urethane rod, finger pressure simulating force applying device.

An artificial finger pressure application device 70 as shown in FIGS. 9A-9C is typically used during production of the overall orthodontic protection device is typically used to apply a finger pressure amount of from 0.2 psi to about 2 psi and force the dry powdered hydrophilic polymeric material(s) to mechanically adhere to at least one (typically one) surface of the extruded base material. The pressure could be slightly more than fingertip pressure of up to about 4 psi as well. The construction of the artificial finger pressure application device 70 is shown in FIGS. 9-11. The artificial finger pressure application device 70 engages the swivel bar 80 using the mounting peg/projection 79, which is engaged with a receiving aperture 81 in the swivel bar 80. The artificial finger pressure application device 70 has a housing 72 that receives the soft urethane artificial finger 74. The housing has an outwardly extending peg 76 that extends along the longitudinal axis of the artificial finger pressure application device 70 and is removably and rotatably engaged, typically by hand and without the use of tools, with a recess 82 in the swivel bar 80. The artificial finger pressure application device 70 is engaged in the processing line to press the dry powder adhesive into the extruded silicone rod after the knurled wheel deposits PVP.

Figure 12:
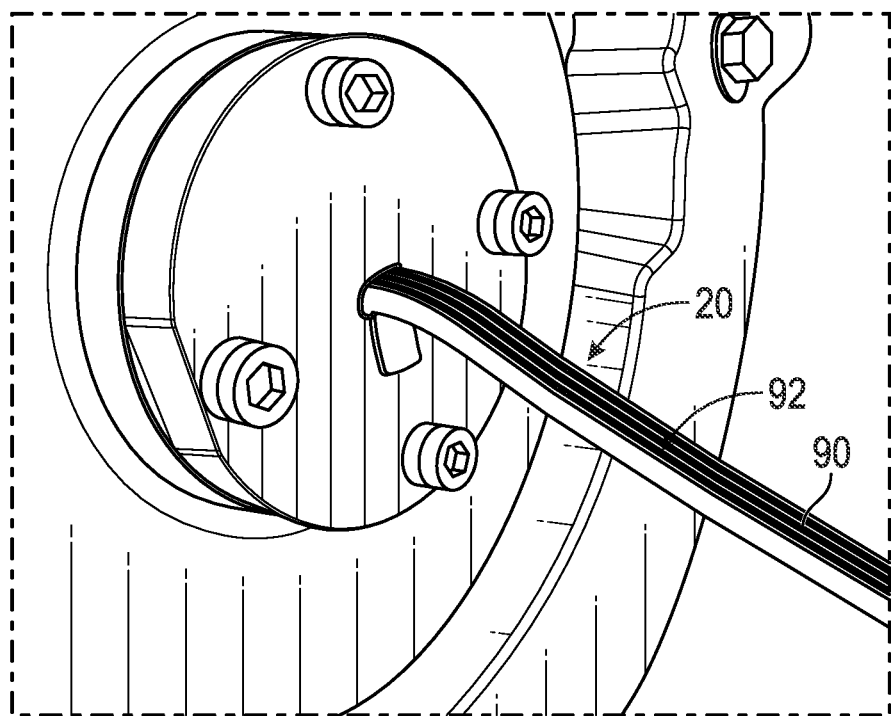
FIG. 12 is a perspective view of the finger force malleable material being extruded to include PVP receiving microgrooves on a top length surface of the base material.
Figure 13:
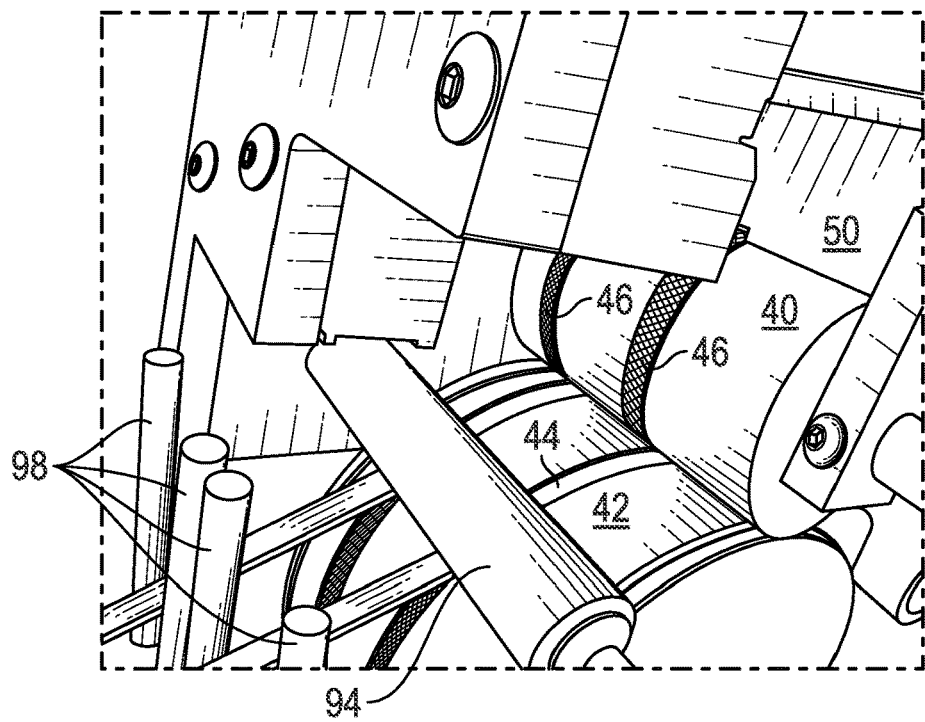
FIG. 13 is a perspective view of the extruded base material entering the application station where hydrophilic polymeric material(s) are applied.
Figure 14:
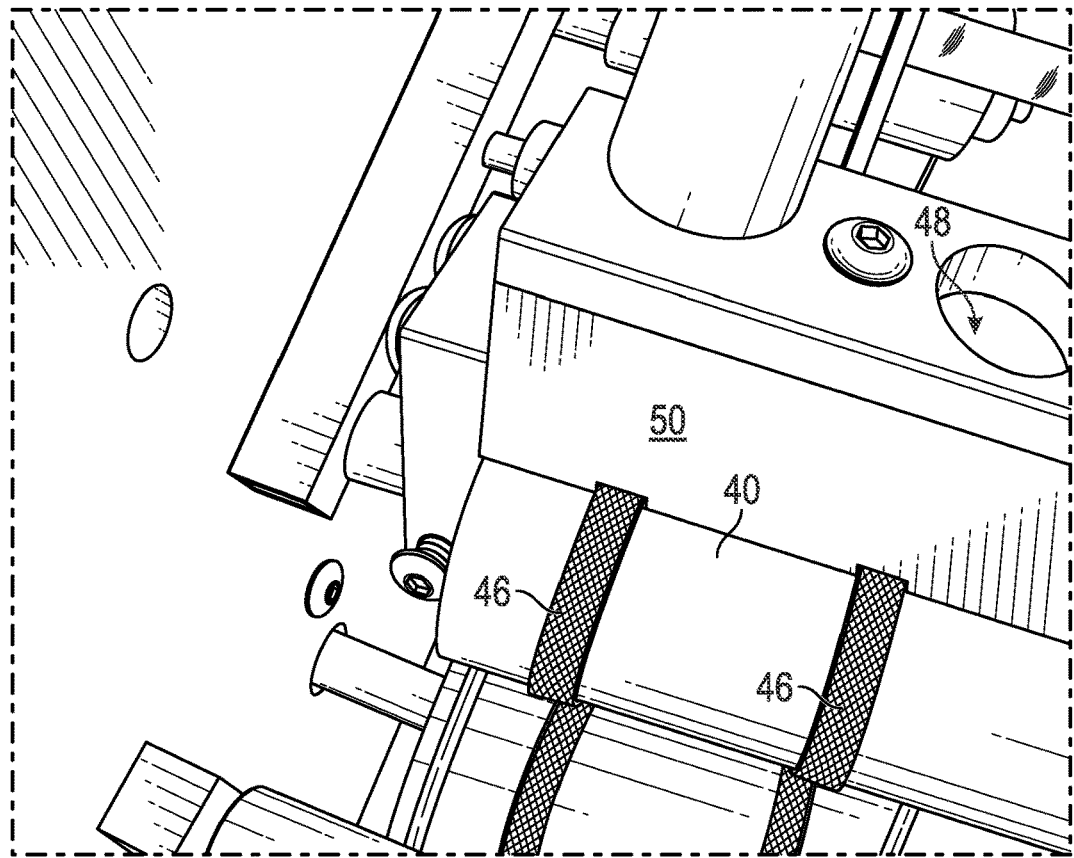
FIG. 14 is a perspective view of the extruded and coated base material departing the application station/system with the hydrophilic polymeric material(s) applied thereto.
Figure 18:
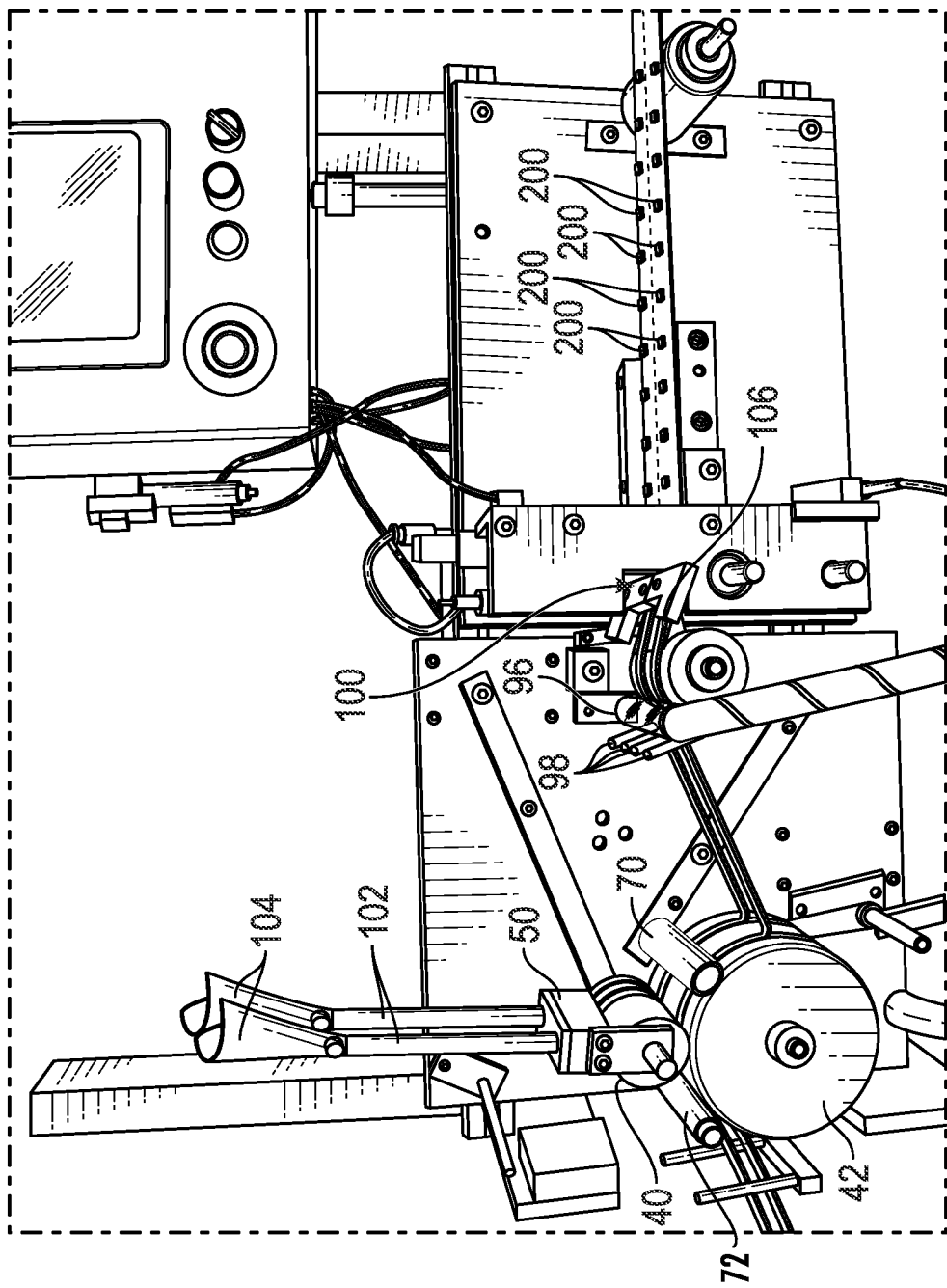
FIG. 18 is a perspective view of an overall system of the present disclosure having two lines of temporary tooth repair compositions being produced simultaneously.
Figure 19A:
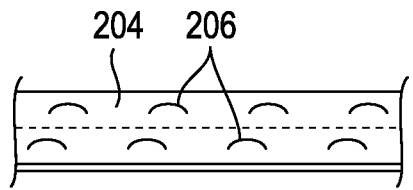
FIG. 19A is a portion of the top film used in the formation of the overall products of the present disclosure that has been through a dimpling process, but not yet placed over the tooth compositions of the present disclosure and heat sealed in individual pockets produced by the dimpler(s) of the present disclosure.
Figure 20:
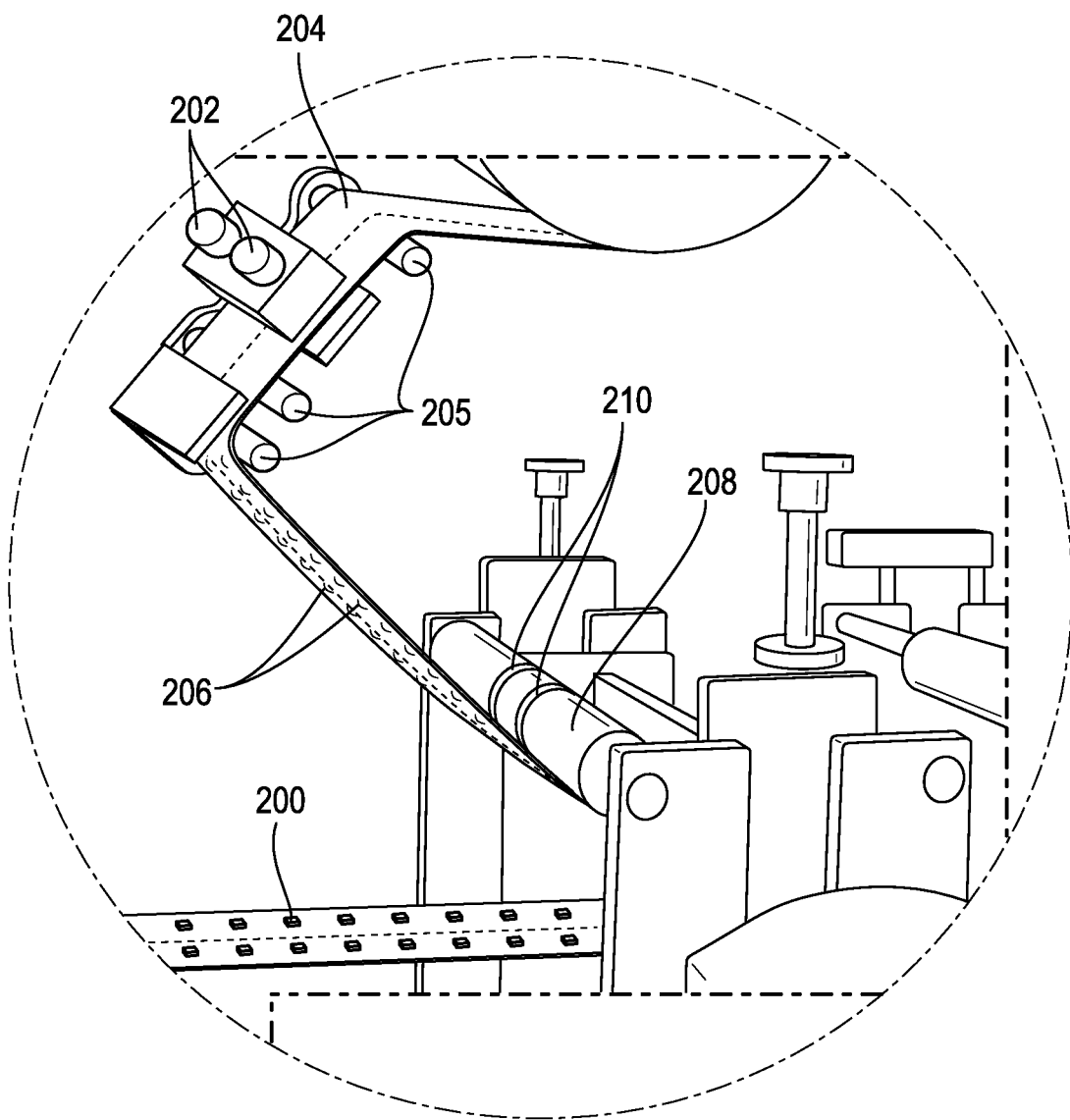
FIG. 20 is an enlarged view of a dimpler system of the present disclosure showing the top material, typically a clear top material to allow visualization of the product within the dimpled portion of the sealed system.

FIG. 12 shows a finger force malleable material being extruded to form dry adhesive receiving microgrooves 90 on a top length surface 92 of the base material 20. Once extruded, the base material 20 proceeds to go under a guide roller 94 (See FIG. 13) and into the larger extruded base material receiving roller 42. The grooved base material is fed into the groove(s)/channel(s) 44. As shown in FIGS. 13-14, the base material proceeds such that the dry adhesive and/or other hydrophilic polymeric material(s) is applied, typically by gravity at this stage, onto the top surface of the base material from the knurled portion(s) 46. As shown in FIG. 18, the dry adhesive, which is typically xanthan gum, and/or other hydrophilic polymeric material(s) are typically delivered from a funnel 104 or other container spaced above the knurled portion(s) such that the dry adhesive and/or other hydrophilic polymeric material(s) are delivered by gravity through the downspout 102 of the funnel 104 and into the knurled portion(s) which then deliver the dry adhesive and/or other hydrophilic polymeric material(s) to the base material.

Figure 15:
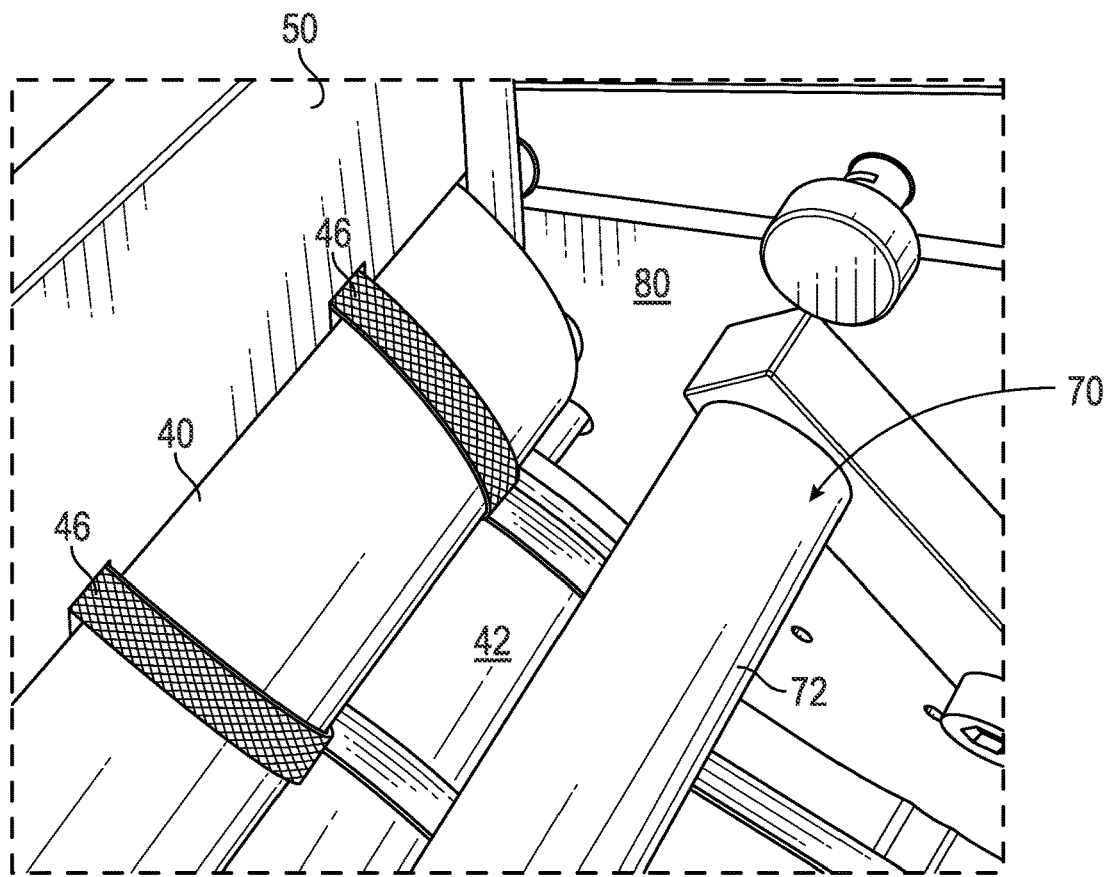
FIG. 15 is a perspective view of the pressure applicator system applying pressure, typically finger pressure, to the loose dry hydrophilic polymeric material(s) to place the loose dry hydrophilic polymeric material(s) into frictional engagement with the base material.
Figure 16:
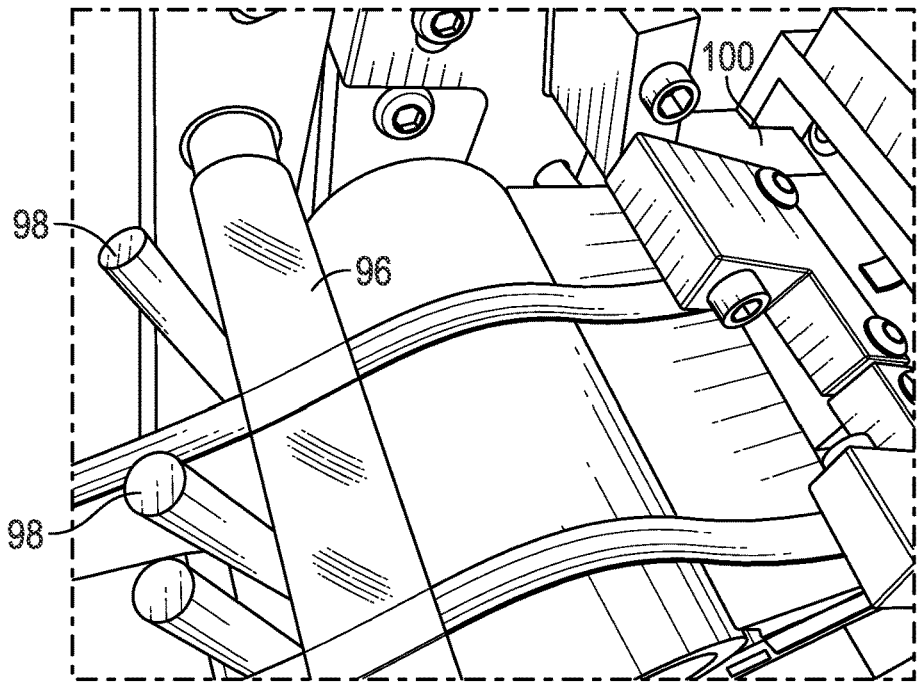
FIG. 16 is a perspective view of the vacuum removal system and guillotine cutting system to make predetermined sized temporary tooth repair composition segments in multiple lines simultaneously, in this case, two lines.
Figure 17:
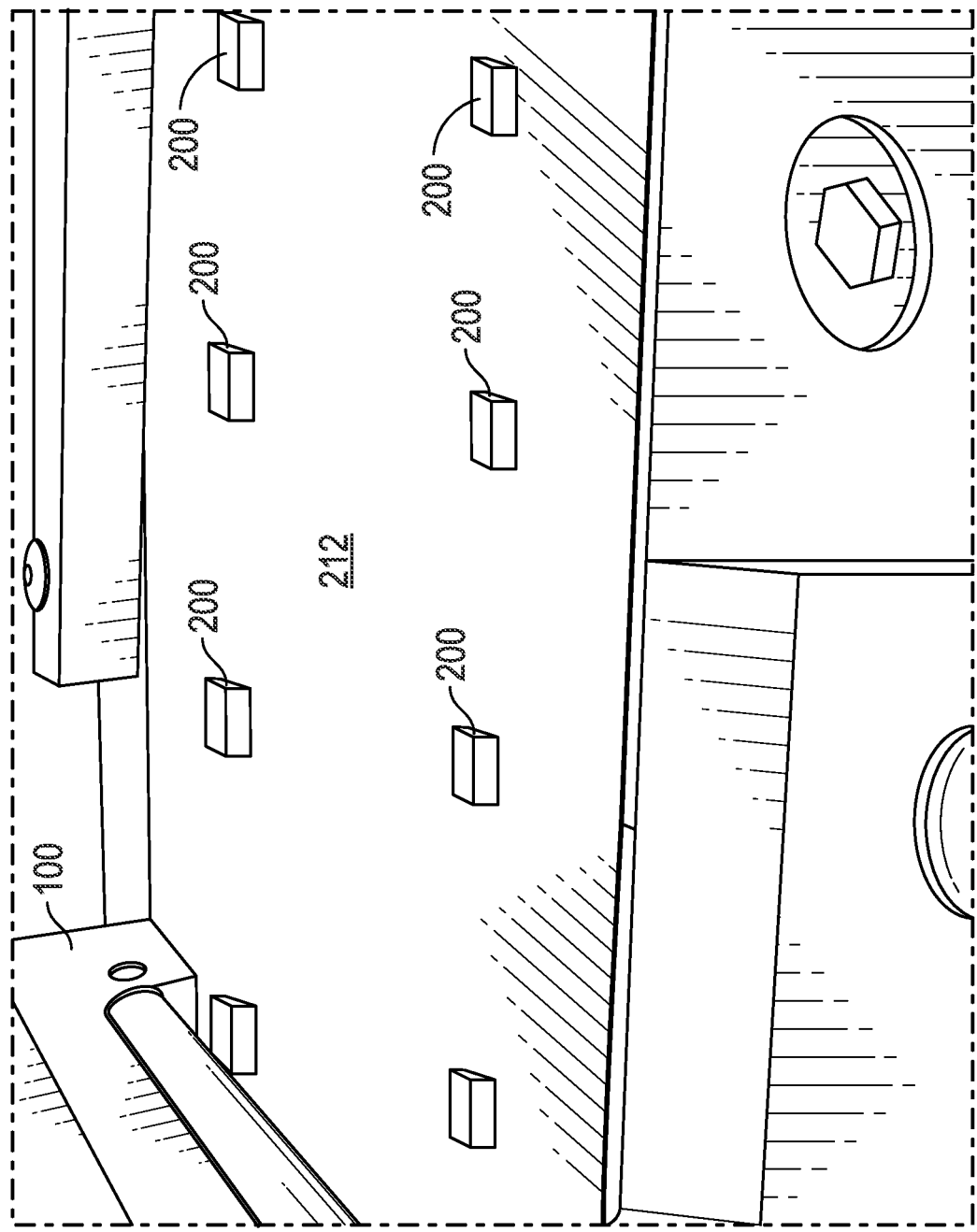
FIG. 17 is a perspective view of the cut and sized temporary tooth repair composition segments traveling along a conveyor belt system to be packaged for use and delivery to the end user. Typically, the devices are packaged in individual tamper evident segments. A plurality of segments may be formed and spaced apart using the same system. Typically, two rows are run side by side, but conceivably any number of rows could be produced if the systems are elongated.

As shown in FIG. 15, the dry adhesive and/or other hydrophilic polymeric material(s) coated base material then is guided under the artificial finger pressure application device 70 such that essentially a pressure in the amount of finger pressure (about 0.2 to about 2 psi or less). FIG. 16 shows the coated base material proceeding under a rod 96 and between two guide posts 98. The rod 96 has a vacuum that removes any loose and not frictionally engaged hydrophilic polymeric material(s) from a surface of the base material. Typically, hydrophilic polymeric material(s), such as xanthan gum, are only applied to one surface to make that surface the user evident surface to be applied to the surface of the tooth/teeth/dental device(s). The vacuum helps remove excess hydrophilic polymeric material(s) from other surfaces the material may be loosely connected to. Once applied by the end user, as discussed above, the base material and the hydrophilic polymeric material(s) become essentially clear or visibly clear to the naked eye. FIG. 17 shows the cut and sized orthodontic protection devices traveling along a conveyor surface 202 to be packaged for use and delivery to the end user. Typically, the cuboid dental compositions 200 are thereafter packaged in individual tamper evident containers.

FIG. 16 also shows the guillotine cutting system 100 that is used to cut the dental compositions of the present disclosure into a predetermined size for each dental composition. Typically, they are in the form of a cuboid dental compositions 200 sized to cover at least one tooth surface; however, the devices can be sized to cover a plurality of teeth. The system typically produces two dental composition cuboids per second (one cuboid per second from each of two rods), but the system could run at a rate as fast as two dental compositions per extruded rod per second utilized instead of one or conceivably at slower speeds as well. The system may also run at one dental composition per 0.66 seconds per extruded rod. In FIG. 18, an acrylic clear tube 102 holding the dry powder adhesive and other optional components (the hydrophilic polymeric material(s)) is shown. Inside and also attached to the acrylic tube downspout 102 will be vibrators (not shown) which actuate, typically at programmable intervals, to make sure the dry powder (the hydrophilic polymeric material(s)) shakes down into the applicator. The large white grooved TEFLON® 42 roller that holds the extruded rod as it receives dry adhesive powder (the hydrophilic polymeric material(s)) applied (typically dropped) onto it also has an adjustable spring attached to the device 70, and a white TEFLON® scraper 106 below to help remove the extruded rod from the groove in the TEFLON® roller 42. You can also see two tubes hooked to a vacuum cleaner. The knurled steel roller that fills with dry adhesive powder (the hydrophilic polymeric material(s)) and transfers it to the extruded rod can be of various depths to the knurls, which in turn controls how much dry adhesive powder (the hydrophilic polymeric material(s)) gets dumped onto the base material (extruded rods). It is part of a black colored roller, which is black because it has been anodized.

A KEYENCE® vision system or similar vision system is typically used in connection with the present systems to ensure that a minimum level of the hydrophobic water insoluble solid material (typically xanthan gum alone or in combination with one or more of the other substances discussed above) is applied by measuring how white the material is leaving the manufacturing device. If there is not sufficient xanthan gum or other powder material applied to the surface, the vision system will identify this state and notify the user of the production device(s) to stop the system and/or add more xanthan gum or other hydrophobic water insoluble solid material(s) to the applicator or the funnel delivery system/hopper so that the hydrophobic water insoluble solid material(s) are available in adequate amounts. Instead of the systems described above, a cable coating system such as the NORDSON™ ECC 702 system may be employed. The applicator uses an electrostatic charge to produce event powder coatings and employ a corona process to charge powder particles with ions from a high voltage source. The powder is fluidized, charged and sprayed onto the cable. Pumps maintain an adjustable, even flow of powder to obtain any desired coating thickness.

As shown in FIGS. 18-21, a unique packaging system is employed as part of the continuous line. The conveyor surface is actually a bottom layer thermoplastic film of the packaging system of the present disclosure. The bottom film 212 is fed off of rolls 214 and guided around guide rollers 215 to bring them underneath the guillotine cutting system where the dental compositions of the present disclosure are placed thereon automatically. The bottom film 212 is typically a polyolefin or polyester or a poly-laminate film that includes a polyolefin or a polyester as one of the layers. The dental compositions are then covered and either heat or pressure sealed within dimples created in a portion of the top film 204. The top film is typically any flexible plastic liner that is a heat sealable or pressure sealable adhesive liner. Such liners will typically incorporate polyesters or polyolefins as the flexible component capable of being dimpled. One such specific liner is ACUOTE™ PK3RES product, which is a silicone coated polyester film exhibiting high strength, flexibility and good chemical resistance. Another liner that may be utilized as the top film 204 is a high barrier aluminum oxide coated laminate of three layers, one that is an aluminum oxide coated polyester, a middle adhesive layer, and a linear low-density sealant on the middle adhesive layer that is available from TECHNIPAQ™. The packaging system of the present disclosure helps prevent harm to the dental composition or any pharmaceutical or food. In the case of the present dental compositions, the dental composition's finger malleable base materials are pliable and susceptible to compressive forces. The packaging system is design to have a stretched portion that, due to the stretching of the top film 204 on only a portion 206 of the top film, significantly lessens the pressure applied to the dental composition when the heat or pressure sealing step is completed and thereby lessens the flattening of the product, which can also drive the surface powder ingredients into the bulk of the silicone, which would decrease their efficacy.

Figure 21:
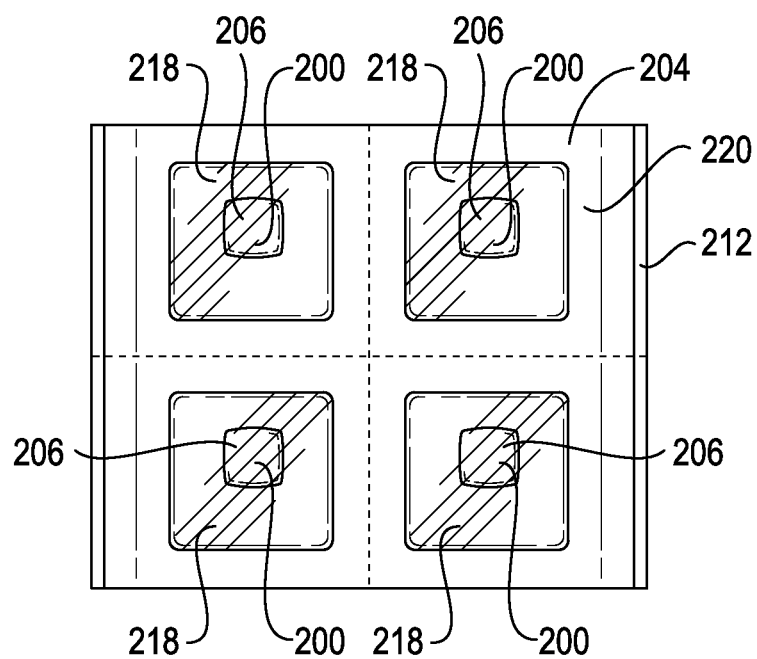
FIG. 21 is a top view of a set of four conjoined single, hygienically packaged products.

The packaging system delivers the top film 204 from the main roll 216 of top film 204 such that the top film travels along and/or around guide rollers 205. Along that path the top film is subjected to a compressive dimpling force from actuators 202. The actuators are typically rods that have a rounded convex end that impact the film. The rounded convex end helps prevent the film from being ripped or torn, which may occur if a rounded surface on the impact member/actuators 202 is not used, when the rods impact the film. As shown in FIG. 21, this dimpling force applied by the rod(s) stretches the film material in a center portion 218 of the end packaging that is aligned to be placed over the composition 200. The dimpled film proceeds to the pressure or temperature sealing system after traveling under the guide roller 208, which has grooves 210 therein that align with the dimpled portions 206 of the top film 204 to prevent flattening or damage to the dimpled portion of the film. The top film 204 is placed over the dental compositions that are traveling on the bottom film 212 such that each dental composition is positioned within the volume defined by the dimpled portion of the top film. Thereafter, heat or pressure is applied to the area 220 around each of the dental compositions to hygienically seal the dental composition within a larger cavity 218 than what would be created if the dimpling has not been created. As a result, the malleable dental composition that is somewhat susceptible to compression, is not compressed or flattened in a significant manner which might have otherwise affected the functionality of the dental composition.

Another aspect of the present disclosure includes dental compositions that are provisional (temporary), moisture curable dental cement compositions. The dental cement compositions of the present disclosure may be temporary, moisture-curable, dental cement compositions that have the properties of being malleable and extrudable such that the composition can be extruded into rods through a die opening using the systems described above. The dental cement compositions of the present disclosure in the form of extruded rods also typically have the ability to support its own weight and hold its shape while being passed over rollers and cut into smaller pieces with a cutting blade and deposited onto a moving packaging liner as discussed in connection with other compositions of the present disclosure. The dental cement compositions according to this aspect of the present disclosure are typically free of or at least substantially free of any uncured, uncrosslinked silicone high consistency rubber base material as this material may interfere with the curing of the dental cement composition. The dental cement compositions of the present disclosure may be a dental cement composition of the type typically sold in a small bucket of multiple dose quantity so long as the composition meets the extrudable characteristics contemplated in the context of this aspect of the present disclosure. One such dental cement that may be used is TEMPARIN® brand dental cement sold by DENTEK®. The dental cement composition of the present disclosure may include eugenol or be substantially free or free of eugenol. A eugenol based dental cement contemplated may include the following components: zinc oxide powder; calcium sulfate; petroleum jelly; potassium alum (potassium aluminum sulfate); paraffin, aluminum sulphate, aluminum phosphate, one or more essential oil components such as menthol crystals (which may be removed if the menthol flavoring and other effects are not desired) and eugenol; and yellow iron oxide. The amounts of paraffin and petroleum jelly, which operate as the base materials for the dental cement may be lowered or raised to adjust the extrusion characteristics of the composition. The eugenol and zinc oxide in composition with the moisture present on the tooth or dental component operate to cure and provide the cementing function of the compositions of the present disclosure. The extruded dental cement compositions of the present disclosure further may include an applied surface composition, typically an adhesive composition to which hypersensitivity desensitizing agents may also be added on at least one surface thereof. The surface applied compositions are typically added to further enhance proper and easy adherence of the dental cement composition to a given location and provide a temporary bond until a more permanent albeit still temporary adherence of the dental cement base can cure. Of course, the other functional compositions of the coating compositions of the present disclosure described in connection with the compositions utilizing an uncured, uncrosslinked silicone high consistency rubber base material may be utilized in the coating compositions applied to the extruded dental cement compositions of the present disclosure. Regardless of the extrudable, base dental cement composition(s) employed, the coating compositions, for example, may include one desensitizing ingredient or a plurality of desensitizing ingredients. Significantly, adding xanthan gum, a surface adhesive of the present composition into the base composition of the dental cement compositions It is also presently believed that extrudable dental cement compositions of the present disclosure may also formed by modifying the amounts of the components of paste-like dental compositions currently sold in a small rounded bucket like container such as certain DENTEMP® products that would otherwise not be extrudable without modification. The DENTEMP® Loose Cap & Lost Filling Repair dental cement product is a non-extrudable paste in its form as currently marketed. As currently available on the market, the DENTEMP® Loose Cap & Lost Filling Repair dental cement product is sold in a single, multi-use bucket contain and the composition includes: calcium sulfate, barium sulfate, dimethoxytetraethylene glycol, zinc oxide, eugenol, and an ethylmethacrylate polymer. A related non-extrudable DENTEMP® product, the REFIL-IT® product, is also sold in a single, multi-use bucket container and the composition is a eugenol free product that includes: calcium sulfate, barium sulfate, dimethoxytetraethylene glycol, zinc oxide, ethylmethacrylate polymer, cherry flavor, and acesulfame potassium, which is an artificial sweetener. However, it is presently believed that the DENTEMP® Loose Cap & Lost Filling Repair dental cement composition as well as the REFIL-IT® compositions may be modified by lowering the amount of the solvent component of the dental composition, the dimethoxytetraethylene glycol and increasing the amount of the resin component, the ethylmethacrylate polymer. It is presently believed that such a modification will result in a dental composition that may be extruded through the systems of the present disclosure, cut into individual use segments, optionally coated with a coating composition as disclosed herein in connection with any of the base materials, and packaged using the packaging systems of the present disclosure as well. This allows for the formation of sanitary, single use segments of either coated or uncoated dental cement compositions to be packaged rapidly and safely. Moreover, such compositions may be applied using one's fingers by hand and without the use of tools such as a plastic applicator that is necessary for the current dental cement products one the market.

Each of the different dental composition of the present disclosure may be packaged in multi-unit boxes or other containers that are typically rectangular paper-based boxes such that a plurality of the single use dental composition may be packaged within a single overall boxed packaging. This facilitates the sale and distribution of the multiple units of the dental compositions of the present disclosure. Of course, the dental composition in the sealed systems of the present disclosure could also be provide in single use only packaging at the retail or professional orthodontic offices. It is also conceivable that the dental compositions sealed in the systems of the present disclosure could be dispense on a rolled system similar to a toilet paper roll and any number of user selected amounts removed for use or distribution at one time. Perforations typically exist around the side(s) of the seal around each of the dental compositions to facilitate removal of one use of the dental composition from others on a same sheet of base layer film.

What is claimed is:

1. A hygienically packaged composition comprising:
   a base layer of a thermoplastic film;
   a covering film layer that is a heat sealable or pressure sealable adhesive liner that covers the hygienically packaged composition wherein the hygienically packaged composition is chosen from the group consisting of a dental composition, a food composition, or a medicine and wherein the covering film layer comprises a stretched dimple in only a portion of the covering film layer proximate the hygienically packaged composition thereunder the covering film layer; and
   a heat or pressure seal between the base layer and the covering film layer and around each hygienically packaged composition such that there is a space between the heat or pressure seal and the hygienically packaged composition and wherein the hygienically packaged composition is an individual use composition and the stretched dimple is located over the hygienically packaged composition.

2. The hygienically packaged composition of claim 1, wherein the thermoplastic film is a polyolefin or a polyester or a poly-laminate film that includes a polyolefin or a polyester as one layer of the thermoplastic film and wherein the hygienically packaged composition is a solid composition that is not compressed or flattened in a manner that affects a functionality of the solid composition.

3. The hygienically packaged composition claim 1, wherein the covering film layer is a barrier to bacteria and virus and is a flexible plastic material and wherein the hygienically packaged composition is a dental composition that is sealed within a volume between the base layer of the thermoplastic film and the covering film layer and wherein the dental composition is a tooth desensitizing dental composition having a surface composition on a surface of the tooth desensitizing dental composition wherein the surface composition comprises potassium nitrate in an amount up to about 5% by weight of the surface composition and stannous fluoride in an amount up to about 5% by weight of the surface composition.

4. The hygienically packaged composition of claim 3, wherein the surface comprises potassium nitrate in an amount from about 0.01% by weight of the surface composition to about 0.5% by weight of the surface composition and stannous fluoride in an amount of from about 0.01% by weight of the surface composition to about 0.5% by weight of the surface composition.

5. The hygienically packaged composition of claim 3, wherein the covering film layer comprises polyesters or polyolefins and wherein the surface composition comprises potassium nitrate in an amount from about 0.01% by weight of the surface composition to about 0.5% by weight of the surface composition and stannous fluoride in an amount of from about 0.01% by weight of the surface composition to about 0.5% by weight of the surface composition.

6. The hygienically packaged composition of claim 1, wherein the hygienically packaged composition is a dental composition and the dental composition is at least substantially cuboidal shaped having an exterior facing surface and wherein the dental composition adheres to a damaged tooth surface that is wet with saliva within about 8 seconds and wherein the dental composition is chosen from the group consisting of:
   an extrudable dental cement composition that is extrudable through a die at a temperature of from about 10°C to about 50° C.;
   an extrudable base material that is extrudable through a die at a temperature of from about 10°C to about 100° C.;
   wherein the extrudable base material comprises at least one compound chosen from the group consisting of:
      (A) a product consisting of one or more hydrocarbon-based waxes and optionally also one or more inorganic fillers, one or more organic fillers, or one or more inorganic fillers and one or more organic fillers;
      (B) an uncured, uncrosslinked silicone high consistency rubber base; and
      (C) a hydrophobic water insoluble solid material that is malleable at 37° C. or lower and safe for a human oral environment; and
   wherein the extrudable base material has a surface composition applied thereon wherein the surface composition comprises: potassium nitrate, stannous fluoride, and at least one dry, powdered hydrophilic polymeric substance engaged with and dispersed on one or more surface of the extrudable base material.

7. The hygienically packaged composition of claim 6, wherein the at least one dry, powdered hydrophilic polymeric substance is chosen from the group consisting of: a polyvinylpyrrolidone, a polyoxazoline, a polyethylene glycol, a starch, a polyacrylic acid, a carbomer, a polyvinyl alcohol, a polyvinyl acetate, a cellulose derivative, a polysaccharide, a polyacrylamide, a N-vinyl caprolactam polymer, a copolymer of methyl vinyl ether and maleic anhydride (PVM/MA), and blends of any of the above and the wherein the surface composition comprises potassium nitrate in an amount from about 0.01% by weight of the surface composition to about 0.5% by weight of the surface composition and stannous fluoride in an amount of from about 0.01% by weight of the surface composition to about 0.5% by weight of the surface composition.

8. The hygienically packaged composition of claim 6, wherein the at least one dry, powdered hydrophilic polymeric substance consists of a polysaccharide and the polysaccharide is a xanthan gum, a pectin, a guar gum that has been partially hydrated to greater than 12% by weight water but still in powder form, a starch, or a cellulose ether.

9. The hygienically packaged composition of claim 7, wherein the dental composition is finger force malleable at room temperature and the dental composition further comprises a colorant and wherein the covering film layer has a perimeter and a portion of the base layer extends beyond the perimeter of the covering film layer.

10. The hygienically packaged composition of claim 6, wherein the dental composition is the extrudable base material and the extrudable base material has a textured surface and wherein the surface composition is mechanically engaged with and dispersed on the textured surface of the extrudable base material.

11. The hygienically packaged composition of claim 10, wherein the extrudable base material is a cuboid and has the surface composition on a totality of only one surface thereof.

12. The hygienically packaged composition of claim 6, wherein the dental composition is at least substantially a cuboid shape having a first substantially planar surface and wherein the surface composition is mechanically engaged to the extrudable base material and dispersed over an entirety of a surface area of the first substantially planar surface.

13. The hygienically packaged composition of claim 6, wherein the dental composition is configured to adhere to exposed dentinal tubules and the dental composition is at least substantially cuboidal shaped and has at least one exterior facing surface and wherein the dental composition comprises the surface composition applied to the at least one exterior facing surface and wherein the dental composition adheres to a damaged tooth surface that is wet with saliva within about 8 seconds.

14. The hygienically packaged composition of claim 13, wherein the at least one dry, powdered hydrophilic polymeric substance is chosen from the group consisting of: a polyvinylpyrrolidone, a polyoxazoline, a polyethylene glycol, a starch, a polyacrylic acid, a carbomer, a polyvinyl alcohol, a polyvinyl acetate, a cellulose derivative, a polysaccharide, a polyacrylamide, a N-vinyl caprolactam polymer, a copolymer of methyl vinyl ether and maleic anhydride (PVM/MA), and blends of any of the above.

15. The hygienically packaged composition of claim 13, wherein the at least one dry, powdered hydrophilic polymeric substance is a xanthan gum, a pectin, a guar gum that has been partially hydrated to greater than 12% by weight water but still in powder form, a starch, or a cellulose ether.

16. The hygienically packaged composition of claim 13, wherein the at least one dry, powdered hydrophilic polymeric substance comprises one or more water-soluble polymeric adhesive.

17. The hygienically packaged composition of claim 13, wherein the dental composition has a textured surface thereon and the at least one dry, powdered hydrophilic polymeric substance is mechanically engaged with and dispersed on the textured surface of the dental composition.

18. The hygienically packaged composition of claim 6, wherein the dental composition comprises a plurality of individual dental compositions each separately hygienically sealed and connected with one another and sharing the same layer of the thermoplastic film and sharing the same covering layer and wherein a series of perforations to facilitate disengagement of one packaged dental composition from the plurality of individual dental compositions is present in a space between each of the plurality of individual dental compositions while not present on the seal between the layer of the thermoplastic film and the covering layer.

19. A hygienically packaged composition having an interior that contains the hygienically packaged composition wherein the hygienically packaged composition is chosen from the group consisting of a dental composition, a medicine, and a food composition, wherein the hygienically packaged composition comprises a base layer with a base layer perimeter portion and a base layer interior facing portion and a top layer having a top layer perimeter portion and a top layer interior facing portion wherein (1) the base layer interior facing portion, (2) the top layer interior facing portion, or (3) both of the base layer interior facing portion and the top layer interior facing portion are flexed to create a stretched film portion of the base layer interior facing portion, a stretched film portion of the top layer interior facing portion, or both a stretched film portion of the base layer interior facing portion and a stretched film portion of top layer interior facing portion and wherein the base layer perimeter portion and the top layer perimeter portion are heat sealed or pressure sealed together along the top layer perimeter portion and the base layer perimeter portion to create a cavity having a cavity perimeter and wherein the hygienically packaged composition is positioned between the base layer interior facing portion and the top layer interior facing portion and within the cavity and proximate the stretched film portion of the base layer interior facing portion, the stretched film portion of the top layer interior facing portion, or both the stretched film portion the base layer interior facing portion and the stretched film portion of top layer interior facing portion; and wherein the hygienically packaged composition is spaced away from the cavity perimeter of the cavity.

20. At least one hygienically packaged tooth desensitizing dental composition comprising:
 a base layer that is a thermoplastic film;
 a covering film having a surface area wherein the covering film is a heat sealable or pressure sealable adhesive liner that covers a solid tooth desensitizing dental composition and having a flexed and thinner dimpled surface area positioned over the solid tooth desensitizing dental composition;
 a hygienic seal around the solid tooth desensitizing dental composition that creates a cavity having a cavity perimeter between the base layer and the covering film wherein the cavity contains the solid tooth desensitizing dental composition and wherein the solid tooth desensitizing dental composition is spaced away from the cavity perimeter and is not compressed or flattened in a manner which affects a functionality of the solid tooth desensitizing dental composition; and
 wherein the solid tooth desensitizing dental composition has a coating composition applied to at least one surface thereof that comprises (1) potassium nitrate in an amount of from about 0.15 to about 0.5 weight percent of the coating composition (2) stannous fluoride in an amount of from about 0.15 to about 0.5 weight percent of the coating composition and (3) at least one dry, powdered hydrophilic polymeric component that is chosen from the group consisting of: a polyvinylpyrrolidone, a polyoxazoline, a polyethylene glycol, a starch, a polyacrylic acid, a carbomer, a polyvinyl alcohol, a polyvinyl acetate, a cellulose derivative, a polysaccharide, a polyacrylamide, a N-vinyl caprolactam polymer, a copolymer of methyl vinyl ether and maleic anhydride (PVM/MA), and blends.

* * * * *